(12) United States Patent
Padurariu et al.

(10) Patent No.: US 12,183,093 B2
(45) Date of Patent: Dec. 31, 2024

(54) DRIVER MONITORING SYSTEM BASED ON VISION CAMERA

(71) Applicant: VEONEER SWEDEN AB, Vargarda (SE)

(72) Inventors: Catalin Padurariu, Iasi (RO); Adrian Homutescu, Iasi (RO)

(73) Assignee: MAGNA ELECTRONICS SWEDEN AB, Vargarda (SE)

( * ) Notice: Subject to any disclaimer, the term of this patent is extended or adjusted under 35 U.S.C. 154(b) by 45 days.

(21) Appl. No.: 18/247,970

(22) PCT Filed: Oct. 1, 2021

(86) PCT No.: PCT/EP2021/077078
§ 371 (c)(1),
(2) Date: Apr. 5, 2023

(87) PCT Pub. No.: WO2022/073864
PCT Pub. Date: Apr. 14, 2022

(65) Prior Publication Data
US 2024/0020991 A1 Jan. 18, 2024

(30) Foreign Application Priority Data
Oct. 8, 2020 (EP) .................................... 20200801

(51) Int. Cl.
*G06V 20/59* (2022.01)
(52) U.S. Cl.
CPC .................................... *G06V 20/59* (2022.01)

(58) Field of Classification Search
CPC ........ G06V 20/59; G06V 10/143; A61B 5/18; G03B 15/05; G03B 17/561; H04N 23/51;
(Continued)

(56) References Cited

U.S. PATENT DOCUMENTS 6,678,001 B1 1/2004 Elberbaum
9,989,835 B1 6/2018 Gomez
(Continued)

FOREIGN PATENT DOCUMENTS

CN 211223358 U 8/2020
DE 112018000024 T5 10/2019
(Continued)

OTHER PUBLICATIONS

International Search and Written Opinion of PCT/EP2021/077078, mailed Jan. 21, 2022.

*Primary Examiner* — Fernando Alcon
(74) *Attorney, Agent, or Firm* — DICKINSON WRIGHT PLLC

(57) ABSTRACT

A driver monitoring system (1) which includes at least one vision device (10). The at least one vision device (10) is positioned in or at an outer housing (7) and pointing to an outside of the outer housing (7). The outer housing (7) is defined by a housing cover (8) and a housing base (9). A housing (20) of the vision device (10) has a first spherical outer contour (21) and a second spherical outer contour (22). The first spherical outer contour (21) and the second spherical outer contour (22) provide in cooperation with the housing base (9) and in cooperation with a mounting element (40) a form and force fitting mount of the vision device (10) in the housing outer (7).

15 Claims, 26 Drawing Sheets

(58) Field of Classification Search
CPC .......... H04N 5/33; H04N 7/181; H04N 7/183; H04N 7/185; H04N 23/54; H04N 23/23
See application file for complete search history.

(56) References Cited

U.S. PATENT DOCUMENTS

| | | |
|---|---|---|
| 11,289,241 B2 | 3/2022 | Kojima et al. |
| 11,400,868 B2 | 8/2022 | Pan |
| 2012/0263450 A1 | 10/2012 | Totani |
| 2017/0115549 A1* | 4/2017 | Wada .................... G03B 17/561 |
| 2017/0237908 A1* | 8/2017 | Ko .......................... H04N 23/57 386/341 |
| 2017/0264796 A1* | 9/2017 | Tian ......................... H05K 5/03 |
| 2018/0222402 A1 | 8/2018 | Bingle et al. |
| 2018/0312113 A1* | 11/2018 | Hirano ................... G08B 21/06 |
| 2020/0096844 A1* | 3/2020 | Liao ...................... G03B 15/006 |
| 2020/0120239 A1* | 4/2020 | Bingleman ...... G08B 13/19632 |
| 2021/0229605 A1 | 7/2021 | Pan et al. |
| 2021/0249153 A1 | 8/2021 | Kojima et al. |
| 2021/0383104 A1* | 12/2021 | Kramer ................... H04N 23/63 |
| 2021/0397863 A1* | 12/2021 | Kose Cihangir .... G06V 40/171 |
| 2022/0038606 A1* | 2/2022 | Grotto ................ G08B 13/1963 |
| 2022/0214601 A1* | 7/2022 | Tiefenbrunn ....... F16C 11/0623 |
| 2023/0023407 A1* | 1/2023 | Garlock ................. H04N 7/183 |
| 2023/0026043 A1* | 1/2023 | Garlock ................. H04N 23/55 |
| 2023/0356728 A1* | 11/2023 | Jain ......................... G06F 3/013 |
| 2023/0375849 A1* | 11/2023 | Harari ................... H04N 23/55 |
| 2024/0214679 A1* | 6/2024 | Hong .................... H04N 23/54 |

FOREIGN PATENT DOCUMENTS

| | | |
|---|---|---|
| EP | 1096452 A1 | 5/2001 |
| JP | 2004112553 A | 4/2004 |
| JP | 2009286167 A | 12/2009 |
| JP | 2018199488 A | 12/2018 |
| WO | 2018/219951 A1 | 12/2018 |
| WO | 2019/127409 A1 | 7/2019 |
| WO | 2019/164724 A1 | 8/2019 |
| WO | 2019/208091 A1 | 5/2021 |

* cited by examiner

DRIVER MONITORING SYSTEM BASED ON VISION CAMERA

CROSS-REFERENCE TO RELATED APPLICATIONS

This application is a 35 U.S.C. § 371 national phase of PCT International Application No. PCT/EP2021/077078, filed Oct. 1, 2021, which claims the benefit of priority under 35 U.S.C. § 119 to European Patent Application No. 20200801.7, filed Oct. 8, 2020, the contents of which are incorporated herein by reference in its entirety.

FIELD OF THE INVENTION

The invention relates to a driver monitoring system. Especially, the driver monitoring system comprises at least one vision device positioned in or at an outer housing and pointing to an outside of the outer housing. The outer housing is defined by a housing cover and a housing base.

DESCRIPTION OF THE BACKGROUND ART

International patent application WO 2019/164724 A1 discloses a camera module assembly. An outer housing for the camera module comprises a front shell with a window and a rear shell. The camera core includes a lens assembly, a sensor assembly, and a sensor housing. The sensor assembly is disposed within the sensor housing, and the sensor housing is fixed to the lens assembly.

International patent application WO 2018/219951 A1 relates to a camera module for a motor vehicle. The camera module is used for driver monitoring in the passenger compartment. The camera module has at least one printed circuit board and a shield for enclosing said printed circuit board. The shield comprises at least a first shielding part and a second shielding part.

U.S. patent application US 2019/208091 A1 discloses a camera module for a vehicular vision system. The camera module includes a metal front housing, a lens holder and a metal rear housing. The front housing houses a printed circuit board having an imager disposed thereat. The lens holder is attached at a front portion of the housing so that a lens assembly is optically aligned with the imager.

U.S. patent application US 2018/222402 A1 discloses a camera housing portion which has an imaging sensor at a base portion of the camera housing portion. A lens system is at a first portion of the camera housing portion. A first circuit board is provided that includes circuitry associated with the imaging sensor, which is disposed at a second circuit board that is in board-to-board electrical connection with the first circuit board. The camera housing portion and a connector portion are joined together to encase the first and second circuit boards.

In general, vision cameras are more and more present in vehicles. They are used for scanning the environment of the vehicle and also the driver and passengers, sending the data to an ECU (electronic control unit) that is processing the data and sending out warnings to the driver or acting on the vehicle brakes. The most advance vision cameras use two cameras working in stereo configuration to output also the distance. An algorithm is used and the ECU receives the distance to the object.

In existing prior art systems, the awareness of a driver is monitored by a driver monitoring system which is based on a vision camera. Accordingly, the vision camera is positioned inside the vehicle in such a manner that the driver is predictably in the middle of a camera field of view. A source of infrared (IR) light is positioned in the vicinity of the vision camera so that, provided natural light is insufficient, the driver is lit in a non-distracting manner. The infrared light is provided by at least one IR diode. As the dissipated power of the IR diodes is high, the heat is mainly transferred to a large cooling dome. The IR diodes are populated on a printed circuit board which is further attached with thermal paste to the cooling dome. In general, the cooling domes are made of metal. The cooling dome is incorporated in the housing of the driver monitoring system.

With different car lines, the required position of an infrared module in the vehicle may differ from car line to car line, in order to keep focus on the driver. In order to function properly, the installation position of the infrared module, included in the driver monitoring system, is made at different angles as well as inside the electronic control unit (ECU) of the driver monitoring system. This is due to the necessity of mounting of the driver monitoring system's ECU in different positions in the vehicle, also if it is mounted on vehicles with steering on the left or right side, but not limited to it. This brings about a diversity of housing and cover parts, so that similar projects do not share the same housings and covers. It may be that ECUs with identical functions and printed circuit boards are different in construction due to that. Consequently, the development, validation and manufacturing cost is therefore high for such a driver monitoring system.

SUMMARY OF THE INVENTION

It is an object of the present invention to provide a driver monitoring system which allows a low force assembly and adjustment of the vision devices of the driver monitoring system, so that the driver monitoring system provides a solution for a wide variety of car lines. Additionally, the inventive driver monitoring system should save costs and reduce the variety of parts of the driver monitoring system.

The above object is achieved by a driver monitoring system for a vehicle which comprises the features described herein.

In an embodiment, the driver monitoring system comprises at least one vision device which is positioned in an outer housing and points to an outside of the outer housing. The outer housing is defined by a housing cover and a housing base. The driver monitoring system comprises another housing which other housing is for the vision device and has a first spherical outer contour and a second spherical outer contour. The first spherical outer contour and the second spherical outer contour provide in cooperation with the housing base and in cooperation with a mounting element a form and force fitting mount of the vision device in the outer housing. Note that in the sense of the present invention, the firstly mentioned outer housing represents the outer housing of the driver monitoring system which houses the at least one vision device and is defined by the housing cover and the housing base, whereas the other, second housing is a smaller housing which houses the vision device. Accordingly, the smaller housing is arranged in the larger outer housing.

The advantage of the form and force fitting mount of the vision device in the outer housing is that an angular adjustment of field of view of the at least one vision device can be changed regarding the viewing direction and/or an illumination direction at any moment, with a chosen increment. Additionally, the vision devices do not require a glue or any other fixation element.

According to an embodiment of the present invention, the first spherical outer contour and the second spherical outer contour of the housing of the vision device are smooth. According to another embodiment, the first spherical outer contour and/or the second spherical outer contour of the housing of the vision device have formed an array of shallow grooves.

The advantage is that the smooth first spherical outer contour and second spherical outer contour allow a defined fixation of the vision device in a form and force fitting manner. In case first spherical outer contour and/or the second spherical outer contour of the housing of the vision device has an array of shallow grooves, there is an additional support for the position fixation of the vision device.

The advantage of the topologies of the housing design of the vision device is that its spherical outer areas mate with a receptacle, which is part of the housing base in an embodiment. The spherical outer area, which is the first spherical outer contour of the vison device, mates with the mounting element. A channel, which is part of the housing of the vision device in a further embodiment, is used for routing a band cable (flex cable) for electrical connection with at least one signal element, for example at least one (infrared) diode.

In case the vision device is an infrared module, the infrared module has a printed circuit board which is hosted, for example, on a parallelepiped dome attached to a main body of the infrared module. A neck of the infrared module is as long as needed in order for the infrared diodes to reach the border of the ECU or go past it. The neck of the infrared module can be used for insertion, orientation or reorientation of the infrared module. The main body of the infrared module is further on denominated as well "housing of the (infrared) vision device". The channel is formed in the housing of the vison device so that the flexible printed circuit board and the band cable can reach the inner side of the outer housing of the driver monitoring system. The length of the band cable may differ based on actual requirements of the driver monitoring system. For cost reasons, it is best that the band cable is already attached to the flexible printed circuit board by the time the infrared module is assembled to the outer housing of the driver monitoring system. Electronic components may be populated on the outer face of the parallelepiped dome next to the infrared diodes and, if needed, as well on the area attached to the neck or even inside the channel.

Preferably, the infrared module is made of good heat conductors, such as aluminium. In a further embodiment, the topologies of the housing of the infrared module have multiple venting holes which may reduce weight, but more importantly increase the convection area. The overall convection area of the infrared module should be designed such that the area around infrared diodes features a temperature consistently above the temperature of the surroundings. One or several cooling holes may be formed inside the body of the infrared module, that is inside the housing and neck, with the benefit of increasing convection area, without affecting the re-orientation capacity of the infrared module.

The vision device may be a vision camera or an infrared module. In most cases, the driver monitoring system has two vision devices installed. One vision device is a vision camera and the other vison device is an infrared module. Additionally, the vision camera and the infrared module may share the same vision device housing design, with at least the first spherical outer contour and the second spherical outer contour of the vision device housing, which enables a similar mounting concept for the vision camera and the infrared module.

According to an embodiment of the invention, the mounting and orientation adjustment of the vision device is carried in that the vision device is first positioned on a receptacle of the housing base. The receptacle has a spherical portion which is in form fitting contact with the second spherical outer contour of the vision device. In a further embodiment, the at least one receptacle has a central pin which reaches into a channel of the vision device. The channel is provided at the second spherical outer contour of the housing of the vision device.

The advantage of the receptacle is that it allows an adjustment of the vision device with regard to orientation. The spherical portion of the receptacle in cooperation with the second spherical outer contour of the vision device allows an easy rotational movement of the vision device. The central pin of the receptacle limits the rotational movement of the vision device so that the vision device cannot rotate about the optical axis, as it is in the case of the vision camera. The central pin functions as a blocking pin for such rotation.

According to an embodiment of the invention, a mounting element of the driver monitoring system is in a form and force fitting contact with the first spherical outer contour of the housing of the vision device. This concept enables a secure mounting of the vision device (for example, vison camera or infrared module) into or to the outer housing, which still opens the possibility of re-orientation.

According to an embodiment of the invention, the mounting element is a flange of the housing cover. The flange has a flexible area with a topology mating the first spherical outer contour of the vision device, when the housing cover and the housing base are conjoined.

The advantage is that the topology (spherical area) of the flange mates with the first spherical outer contour of the housing of the vision device. The flexible area of the flange may provide appropriate tensioning of the vision device at the same time the housing cover is fixed to the housing base. At this time, the housing of the vision device is fixed, and inside the outer housing, the main printed circuit board is fixed to the housing base. The vision device is seated on the housing base, and optionally, a minimal force may be exerted on the vision device via a gripper, so that the vision device does not move during next step or steps of the assembly process. The vision device is oriented to an angular position as per requirements. Then the housing cover is lowered down unto the housing base. As the housing cover begins descent, the flexible flange of the housing cover comes at first into contact with the vision device, and the clamping force of vision device starts to increase. The clamping is achieved when the housing cover fully rests on the housing base. The housing cover is fixed to housing base by whatever conventional means chosen, for example, screwing. The optional gripper is disengaged.

The interference of flexible flange and vision device are chosen by design so that the clamping is sufficient for securing position of the vision device and that flange does not go into plastic deformation. The clamping of the vision device can be better controlled by means of a dedicated screw. The screw is fixing the flange to the housing base, on a dedicated dome that may be part of the flange of the housing base. The dedicated screwing dome is at a corner of the housing base and may serve as a protection against damage of the vision device.

In further embodiments, as the housing cover is fully rested on the housing base, a clamping gap is still open between the flange of the housing cover and screwing dome. Such a nominal gap may be 0.5 mm to 1 mm. As a screw is bringing the flange of the housing cover and the flange of the housing base together, the flexible flange of the housing cover exhibits a deformation and the gap is brought to 0 mm. The vision device is firmly tightened and fixed in the outer housing of the driver monitoring system.

According to a further embodiment of the invention, the mounting element is a flange of the housing cover with a flexible area. The flexible area has a topology which mates the first spherical outer contour of the vision device. For mounting the housing cover to the housing base, the housing cover has an elongation of the flexible area which is joined with a clinching dome of the housing base.

The advantage of the above embodiment is that the screw for conjoining the housing cover and the housing base may be replaced by a clinching operation of the housing cover flange tip inside the outer housing. The clinching dome, in other embodiments the screwing dome, will extend toward the flange of the housing cover, for example, a sheet metal flange. The height and width of the clinching dome or screwing dome can be adjusted to the required need. The geometry for clinching shall feature one or several recesses for clinching. It is not the scope of the current disclosure to propose a clinching topology or tool. With current disclosure, the possibility exists that a clinching tool in the shape of a compound lever (tongs) is used. The flange, for example a sheet metal flange, has one or several faces which are fit for sinking into the recesses in the housing base.

According to another advantageous embodiment, the mounting element has a plurality of flexible fingers each of which with a tip portion. The at least one tip portion is in form and force fitting contact with at least one shallow groove on the first spherical outer contour of the vision device when the housing cover is joined with the housing base.

The advantage of the above embodiment is that the housing cover interacts with the vision device by means of circular array of flexible fingers, which are arranged on a flange. At least one tip of the flexible fingers is the first to get in contact with the first spherical outer contour of the vision device, when the housing cover is lowered down onto the housing base. As the housing cover is fully lowered on the housing base, the spring effect of the flexible fingers of flanges is at its maximum. It is advantageous to use a grooved housing of the vision device, because in this manner, the anti-rotation effect of the housing of the vision device is improved. In addition, a screw may clamp even more the package of the housing cover and the housing base. In case more compactness and spring performance is needed, than instead of the flexible finger geometry, a dedicated "finger washer" may be fixed to the housing cover prior to a final assembly. Such finger washers have several "fingers" and exist as standard market products.

According to another advantageous embodiment, the mounting element has oppositely arranged claw flanges. The claw flanges are in form and force fitting contact with the first spherical outer contour of the vision device when the housing cover is joined with the housing base.

The advantage of the claw flanges is that the claw flanges have teeth, the edges will lightly scratch the outer surface of the vision device and even more block it against unintended rotation. The vision device can have a smooth first and second spherical outer contour or a first and second spherical outer contour with a plurality of grooves. For mounting, a bending tool is lowered down on the claw flanges. The bending tool has a number of bending prongs equal to the number of claw flanges. The vision device serves as counter tool and so the flanges get bent downwards, embracing the first spherical outer contour of the vision device body.

According to an embodiment, the vision device may feature on its outer spherical surface an array of shallow grooves. The shallow grooves can be obtained, for example, by knurling, die casting or cold pressing. These grooves are valuable in particular, because the claw flanges may engage some of the shallow grooves, no matter what angular orientation the vision device may have. In doing so, the edges of the claw flanges will lightly scratch the outer surface of the vision device and even more block it against unintended rotation, as some of claw flanges will interact with its edges with the grooves.

According an embodiment of the invention, the mounting element is a hair pin spring with a spherical contact area. The spherical contact area is in a form and force fitting contact with the first spherical outer contour of the vision device when the hair pin spring is mounted to the housing base.

The advantage of the above embodiment is that a spherical contact area is provided which faces toward the vision device. The clamping force is transferred from the hair pin spring to the vision device. The spherical contact area of the hair pin spring provides an anti-rotation friction after the assembly and prevents a change of vision device installation angle. The spherical contact area of the hair pin spring is an overmolded plastic part, which can provide better friction with a certain graining, texture, ribbed or dotted patterns. The plastic part can be manufactured directly through plastic injection.

At the beginning of the mounting process, the vision device is seated on the receptacle of the housing base. The vision device is oriented to an angular position as per requirements. Optionally, a minimal force may be exerted on the vision device via a gripper, so that the vision device does not move during the mounting process. The hair pin spring is lowered to the vision device. First, pre-guidings of the hair pin spring find the channels of the housing base and start to engage ramps, which are part of the housing base and are provided on either side of the receptacle. Finally, the spherical contact area of the overmolded part of the hair pin spring reaches the top of the vision device. Then the spring arms reach the maximum spread at the tip of the ramps. In this phase, if desired, a lateral force may be exerted from the housing base on a direction perpendicular to the insertion direction. The lateral force is generated by a contact with the outer wall of the housing base channel. Then, the arms are elastically snapping in, while the arms could slightly retreat on the push-in direction. The gripper is disengaged. Finally, the housing cover is lowered down unto the housing base. The housing cover is fixed to the housing base by whatever conventional means chosen, for example, screwing. Optionally, the tips of the arms may be clinched to the outer housing so that the hair pin spring may not be dismounted.

According to a further advantageous embodiment, the mounting element is a sheet spring, preferably a sheet metal spring. The sheet spring comprises an outer half ring and two inner quarter rings. The inner quarter rings embrace the first spherical outer contour of the vision device when the sheet spring is pushed down to the housing base.

The advantage of the above embodiment is that it can be used in cases when space is limited around the vision device. Furthermore, the embodiment may or may not imply the need of an overmolded area in the contact to the vision device. The sheet spring can be made of metal or plastic. A sheet spring, made of plastic, allows easy manufacturing of a spherical contact geometry, however the plastic solution may be limited in clamping force.

According to an embodiment of the invention, the vision device is an infrared module which is mounted in a form and force fitting manner in the outer housing or outside the outer housing. In the case of mounting outside the outer housing, the upper part and the lower part of a pincer have a spherical topology, which are in form and force fitting contact with a first spherical outer contour and a second spherical outer contour of the infrared module.

The advantage of the above embodiment is that the cooling and orientation dome for the IR diodes is no longer part of the housing base. The inventive housing base or outer housing includes a specific "pincer topology" that is fit for retaining the infrared module. The infrared module hosts the printed circuit board, can be used for cooling the infrared diodes, guides the flexible band cable towards the main printed circuit board, allows orientation and reorientation with respect to the outer housing and can be clamped by the housing pincer so that unintended rotation is not possible.

The pincer topology shall be conveniently positioned, at best on the edge of the housing base or outer housing. The proposed housing topology is fit for plastic injection and die casting, for example metal.

BRIEF DESCRIPTION OF THE DRAWINGS

The numerous advantages of the disclosure may be better understood by those skilled in the art by reference to the accompanying figures in which.

DETAILED DESCRIPTION

Figure 1:
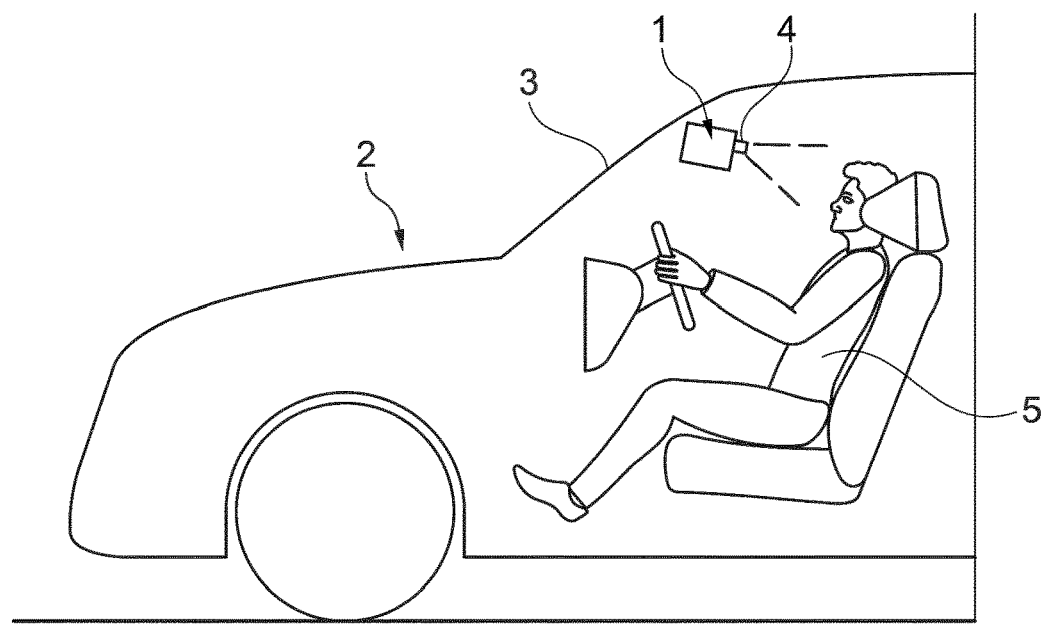
FIG. 1 is a schematic representation of the placement of a driver monitoring system camera according to an embodiment of the prior art.

In the ensuing description, numerous specific details are provided to enable maximum understanding of the embodiments that are provided by way of example. The embodiments may be implemented with or without specific details, or else with other methods, components, materials, etc. In other circumstances, well-known structures, materials, or operations are not illustrated or described in detail so that various aspects of the embodiments will not be obscured. Reference in the course of the present description to "an embodiment" or "one embodiment" means that a particular structure, peculiarity, or characteristic described in connection with its implementation is comprised in at least one embodiment. Hence, phrases such as "in an embodiment" or "in one embodiment" that may recur in various points of the present description do not necessarily refer to one and the same embodiment. Furthermore, the particular structures, peculiarities, or characteristics may be combined in any convenient way in one or more embodiments.

Same reference numerals refer to same elements or elements of similar function throughout the various figures. Furthermore, only reference numerals necessary for the description of the respective figure are shown in the figures. The shown embodiments represent only examples of how the invention can be carried out. This should not be construed as a limitation of the invention.

FIG. 1 shows the arrangement of a driver monitoring system 1 inside a motor vehicle 2 according to an embodiment of the prior art. The driver monitoring system 1 is mounted at or close to a windshield 3 of the motor vehicle 2, so that at least one vision device 10 (see FIG. 2) of the driver monitoring system 1 is looking at a driver 5 of the motor vehicle 2. Especially, a lens 4 of the vision device 10, which is, for example, a vision camera 11, is pointing at the driver 5.

Figure 2:
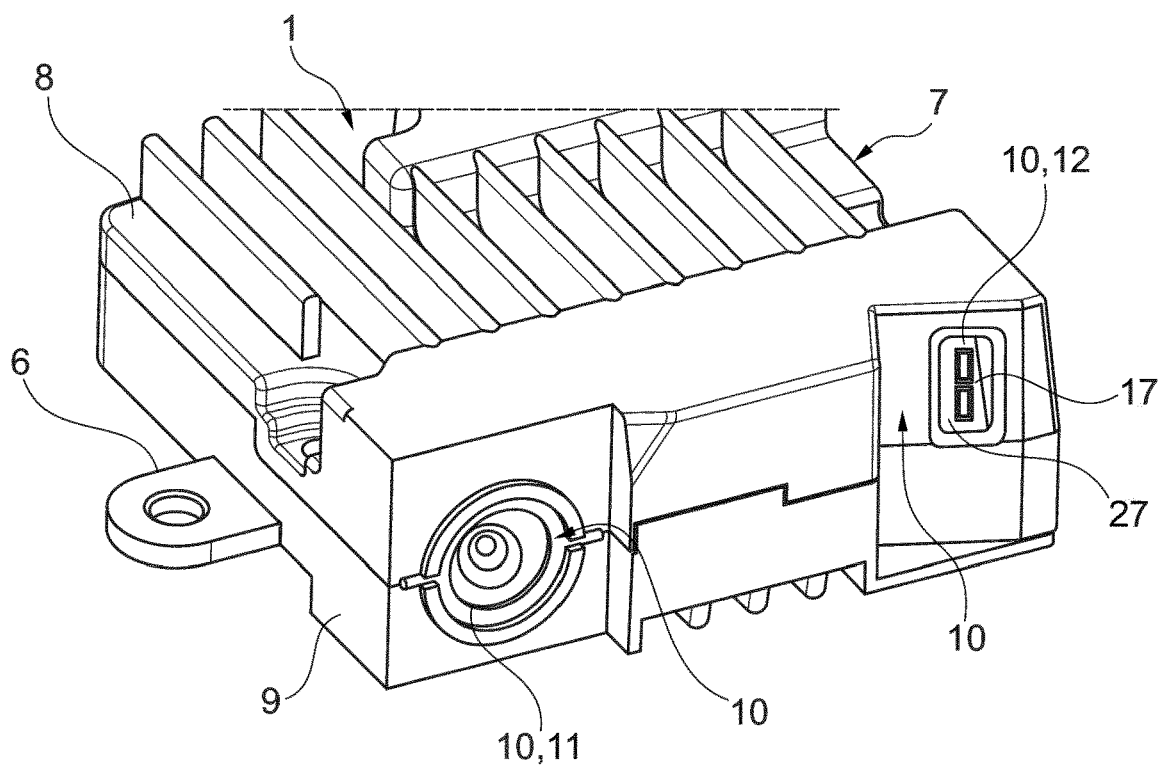
FIG. 2 is a perspective view driver monitoring system with a vision camera module and an infrared module according to the prior art.

FIG. 2 is a perspective view of a driver monitoring system 1 according to an embodiment of the prior art. The driver monitoring system 1 has two vision devices 10, which are a vision camera 11 and an infrared module 12. The vision camera 11 defines a camera window (not shown). The infrared module 12 defines an IR window (not shown). The infrared module 12 of the prior art driver monitoring system 1 has two infrared diodes 17. The number of diodes 17 should not be regarded as a limitation. The driver monitoring system 1 has an outer housing 7 which is composed of a housing cover 8 and a housing base 9. The housing base 9 has at least one mounting ear 6 for fixing the driver monitoring system 1 in the vehicle 2.

Figure 3:
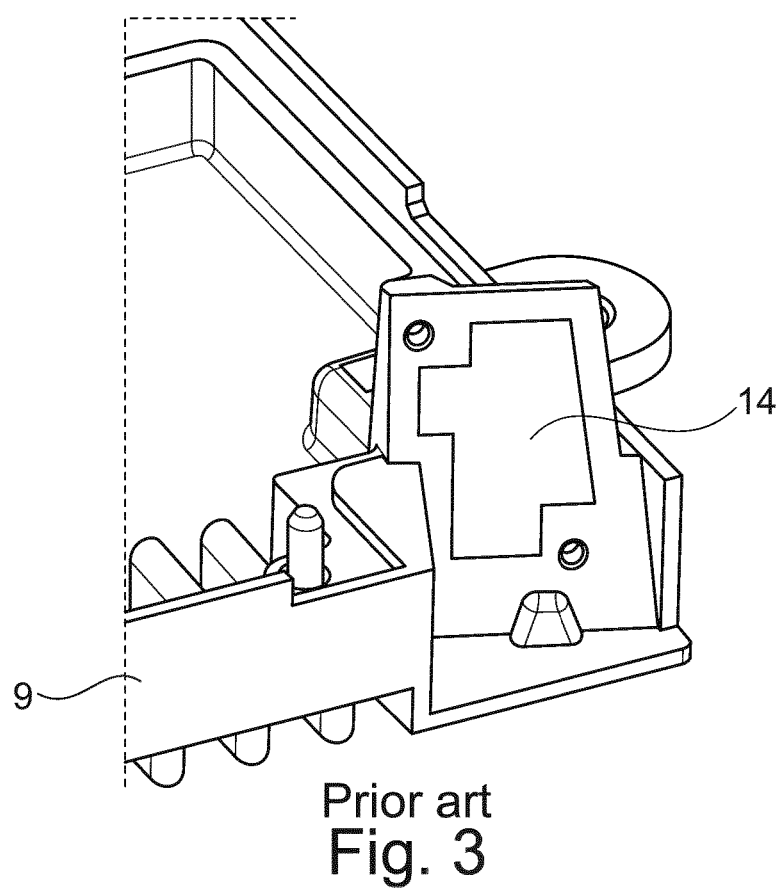
FIG. 3 is an enlarged perspective view of a cooling dome for the infrared illumination module according to the embodiment of prior art.

As the dissipated power of the infrared diodes 17 is high, the heat is preferably mainly transferred to a large cooling element. For example, the enlarged, perspective view in FIG. 3 shows a cooling dome 14 according to an embodiment of the prior art. The cooling dome 14 is used to transport the heat away which is generated by the infrared diodes 17.

Returning to FIG. 2, the driver monitoring system 1 is positioned inside the vehicle 2 in such a manner that the driver's 5 face is predictably in the middle of camera's field of view. The infrared module 12 is positioned in the vicinity of the vision camera 11 so that if natural light is insufficient, the driver is lit in a non-distracting manner by infrared light. The infrared diodes 17 are populated on a printed circuit board 27 which is further attached, for example with thermal paste, to the cooling dome 14. According to the prior art, the cooling dome 14 is made of metal.

Figure 4:
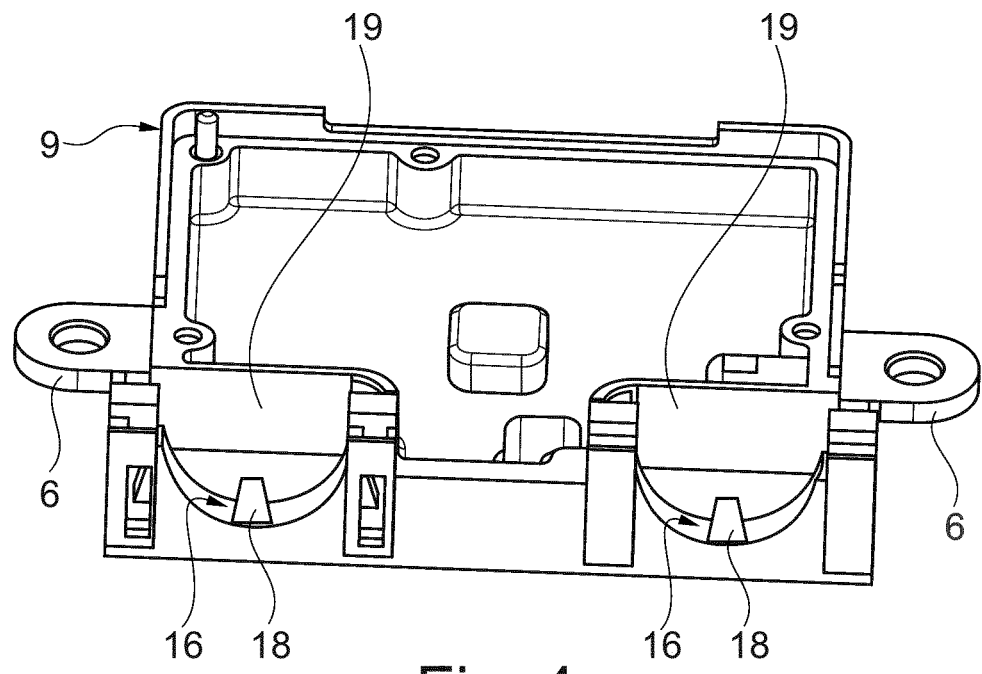
FIG. 4 is a perspective view of an embodiment of the housing base.

FIG. 4 is a perspective view of an embodiment of the housing base 9 for mounting and adjusting two vision devices 10 (one vision camera 11 and one infrared module 12), see FIG. 3. The number of vision devices 10 should not be regarded as a limitation of the invention. The embodiment of the housing base 9 shown here has two receptacles 16, wherein each of which is designed to accommodate one vision device 10. Here, each receptacle 16 has an elastic pin 18 for the fixation of a respective vision device 10. As mentioned above, the mounting ears 6 of the housing base 9 are provided in order to mount the outer housing 7 of the driver monitoring system 1 inside a vehicle. Each receptacle 16 has a wall element 19 which blocks the interior of the housing base 9 and outer housing 7, respectively from the ingress of dust, dirt or the like. The housing base 9 and the housing cover 8 can be manufactured of sheet metal. No holes or slots are provided in housing base 9 and the housing cover 8, so that no passage for water (dripping) or radiation (EMC issues) is possible.

Figure 5A:
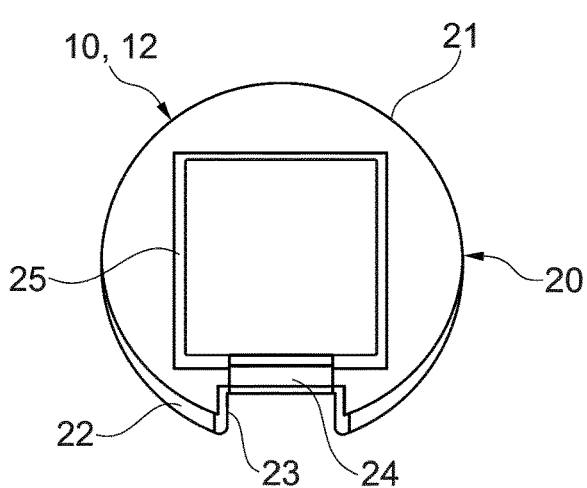
FIGS. 5A to 5C are various views of an embodiment of the vision device.
Figure 5B:
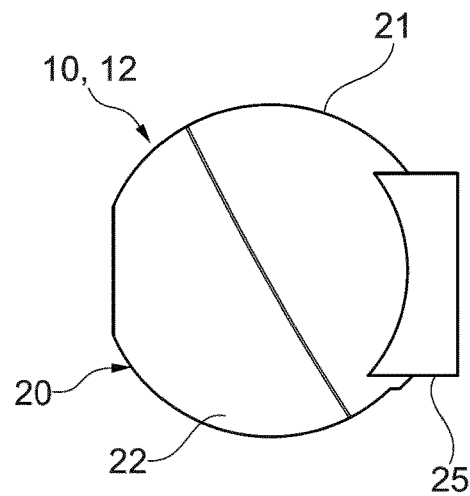
Figure 5C:
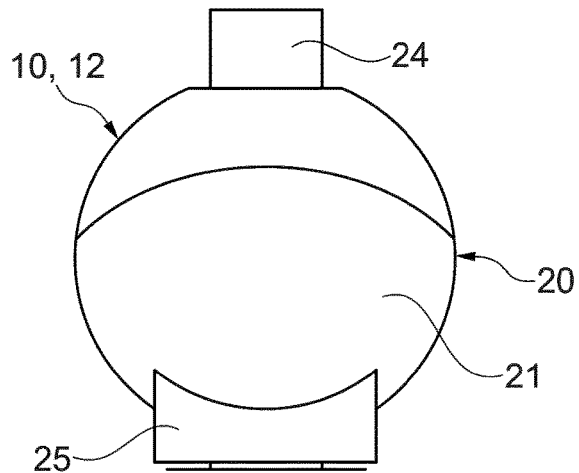

FIGS. 5A to 5C show different views of an embodiment of the vision device 10. The vision device 10 is designed to have a housing 20 with a first spherical outer contour 21 and a second spherical outer contour 22. Note that in the sense of the present invention, outer housing 7 represents the outer housing of driver monitoring system 1 which houses the at least one vision device 10 and is defined by the housing cover 8 and the housing base 9, whereas housing 20 is the smaller housing which houses a single vision device 10. Accordingly, the smaller housing 20 is arranged in the outer housing 7. In the embodiment shown here, the vision device 10 is an infrared module 12. A channel 23 is formed in the housing 20. A band cable 24 is guided in channel 23. A neck 25 of the housing 20 accommodates the infrared diodes (not shown here).

Figure 6A:
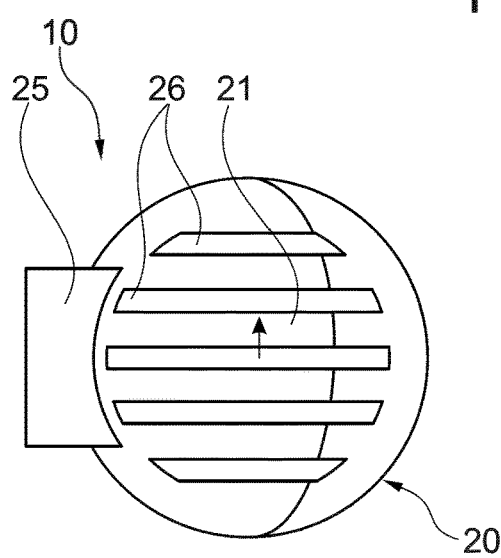
FIGS. 6A and 6B are various views of a further embodiment of the vison device.
Figure 6B:
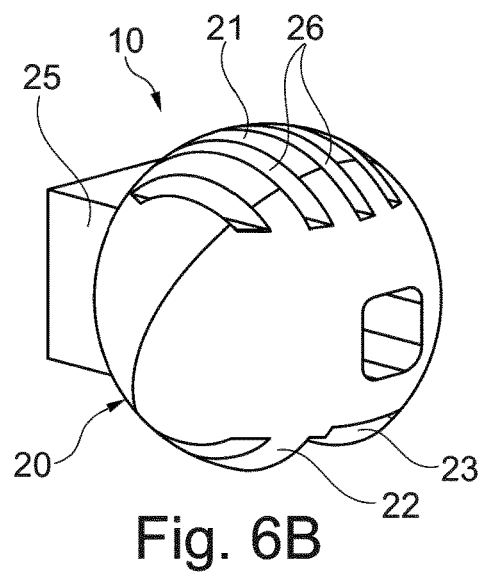

FIGS. 6A and 6B show various views of a further embodiment of the vison device 10. As mentioned above, the vision device 10 comprises a first spherical outer contour 21 and a second spherical outer contour 22. In this embodiment, one or several cooling fins 26 are part of the housing 20. The cooling fins 26 are formed such that they do not disturb the first spherical outer contour 21 and the second spherical outer contour 22. Furthermore, the cooling fins 26 lead to an increasing convection area without affecting the re-orientation capacity of the vision device 10.

Figure 7A:
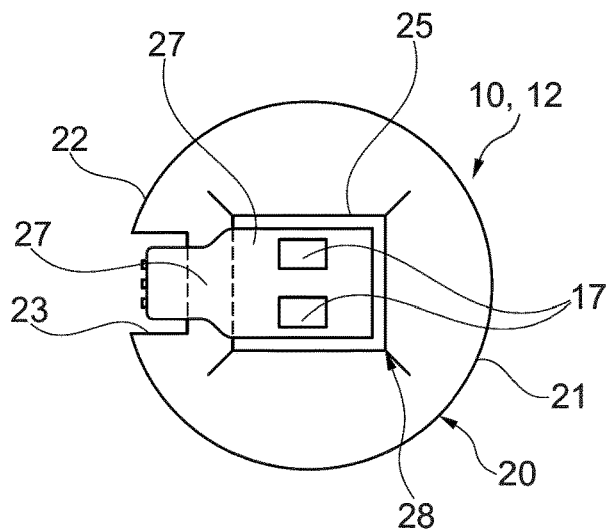
FIGS. 7A to 7C are various views of a further embodiment of the vision device in the form of an infrared module for illumination.
Figure 7B:
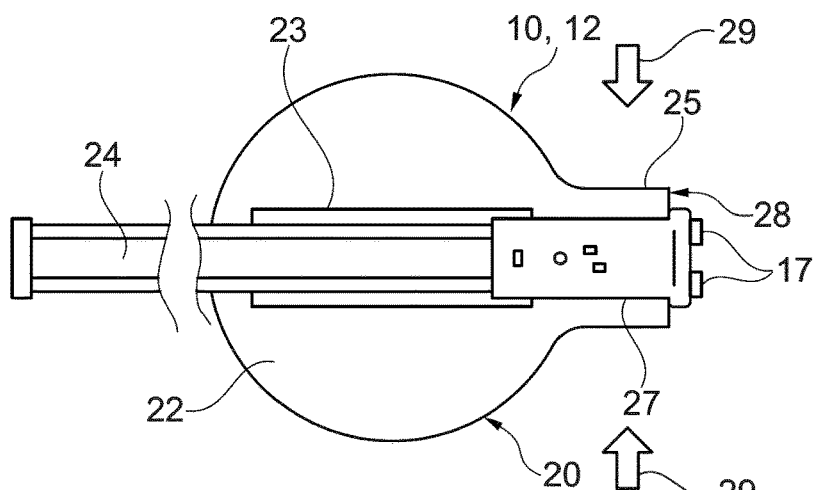
Figure 7C:
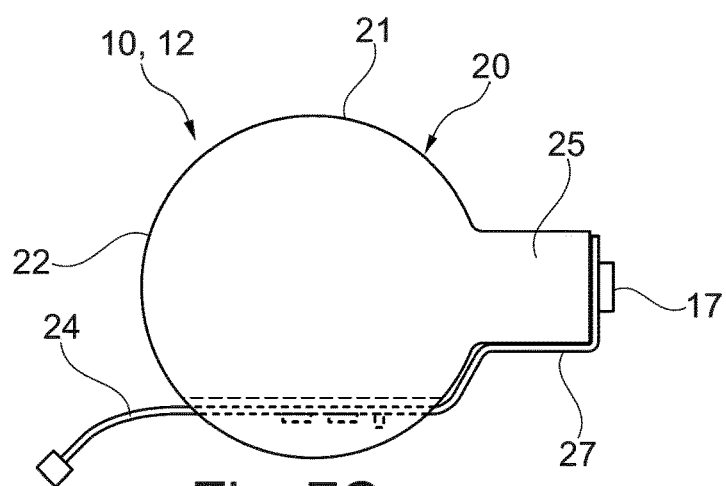

FIGS. 7A to 7C are various views of a further embodiment of the vision device 10 in the form of an infrared module 12 for illumination with IR light in case the ambient light conditions are not sufficient for obtaining an image of the driver. The housing 20 of the vision device 10 has a neck 25 and on a free end 28 where the infrared diodes 17 are placed. The infrared diodes 17 are positioned on a flexible printed circuit board 27, which is hosted by the housing 20. The cooling of the infrared diodes 17 is carried out through flexible printed circuit board 27 which is in contact with the housing 20. Consequently, the vision device 10 in the form of an infrared module 12 should preferably be made of a good heat conducting material, for example aluminium. The flexible printed circuit board 27 is connected via the band cable 24 to a printed circuit board (not shown here) in the outer housing 7 of the driver monitoring system 1. The arrows 29 in FIG. 7B show possible faces of the neck 25 fit to be used in insertion, orientation or reorientation of the infrared module 12.

Figure 8:
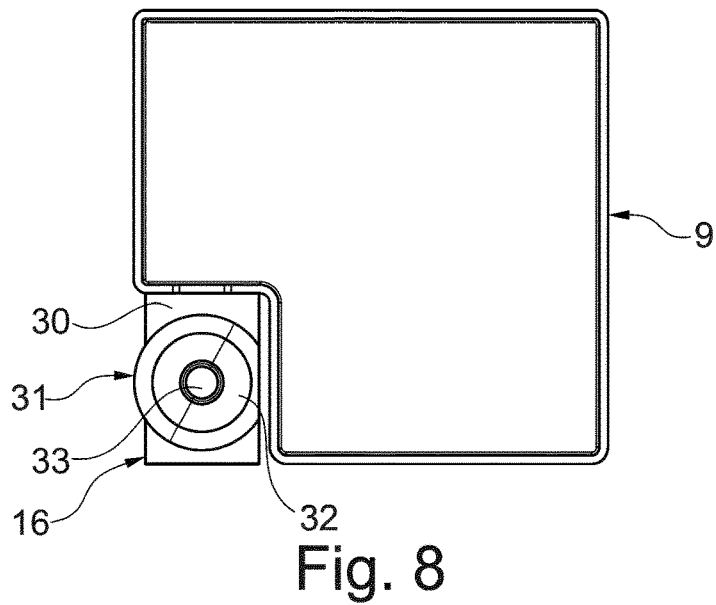
FIG. 8 is a top view of an embodiment of the housing base.

FIG. 8 is a top view of one embodiment of the housing base 9. Here, the receptacle 16 of the housing base 9 is defined by a flange 30 with a siting surface 31 for the vision device 10 (for example, vision camera 11 or infrared module 12). The siting surface 31 is defined by a spherical portion 32 and a central pin 33. The spherical portion 32 has a form so that it can have a form fitting relationship with the second spherical outer contour 22 of the vision device 10. The central pin 33 can block the free movement of the vision device 10 siting on the siting surface 31 of flange 30.

Figure 9A:
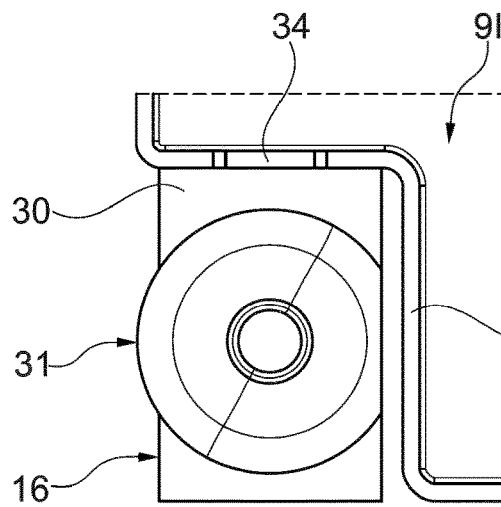
FIGS. 9A and 9B are various detailed views of an embodiment of the receptacle for the vision device of the housing base.
Figure 9B:
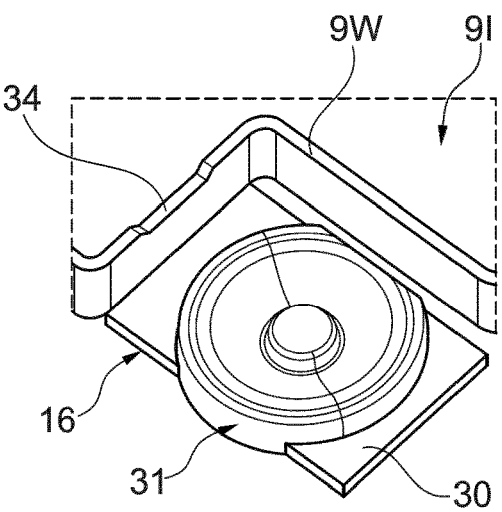

FIGS. 9A and 9B show various detailed views of the receptacle 16 for the vision device 10. The flange 30 of the housing base 9 (see FIG. 8) is separated from the inner portion 9I of the housing base 9 by a surrounding wall 9W. The surrounding wall 9W has a passage 34 formed therein, which allows the guidance of the band cable 24 (see for example FIG. 7B) into the interior portion 9I of the housing base 9.

Figure 10:
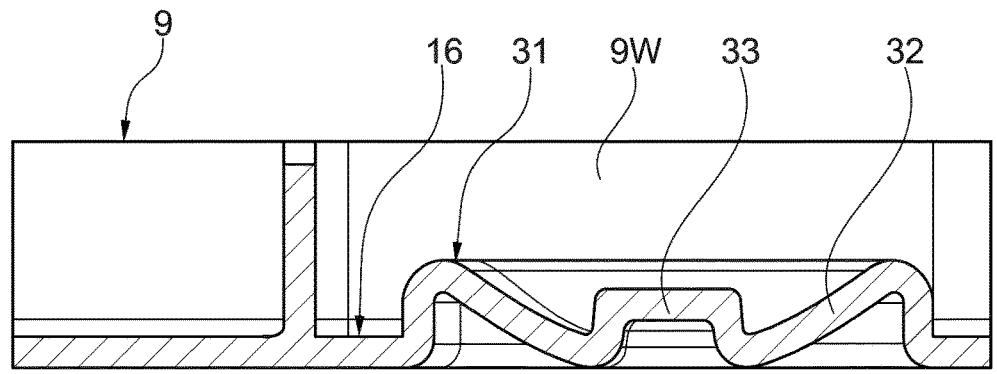
FIG. 10 is a sectional view of the portion of the housing base with the receptacle for the vision device.
Figure 13:
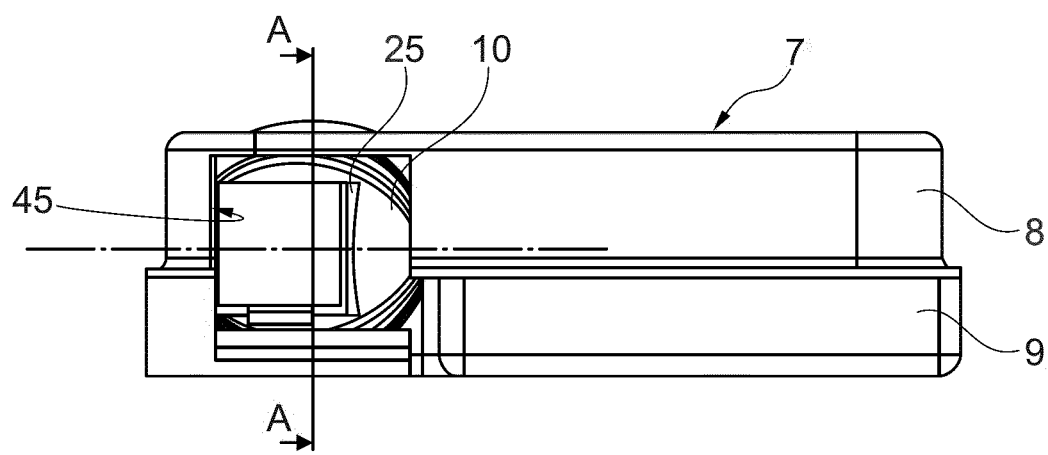
FIG. 13 is a side view of the driver monitoring system, wherein the vision device is mounted between the housing base and the housing cover.

FIG. 10 is sectional view of a portion of the housing base 9 with the receptacle 16 for the vision device 10 (not shown here). The spherical portion 32 of the siting surface 31 surrounds the central pin 33. The wall 9W separates the inner portion 9I (see FIGS. 9A and 9B) of the housing base 9 from the receptacle 16. From the description of FIGS. 8 to 10 one recognizes that the housing base 9 and the housing cover 8 (see for example FIGS. 13 and 14) are best fit for a die cast technology.

Figure 11:
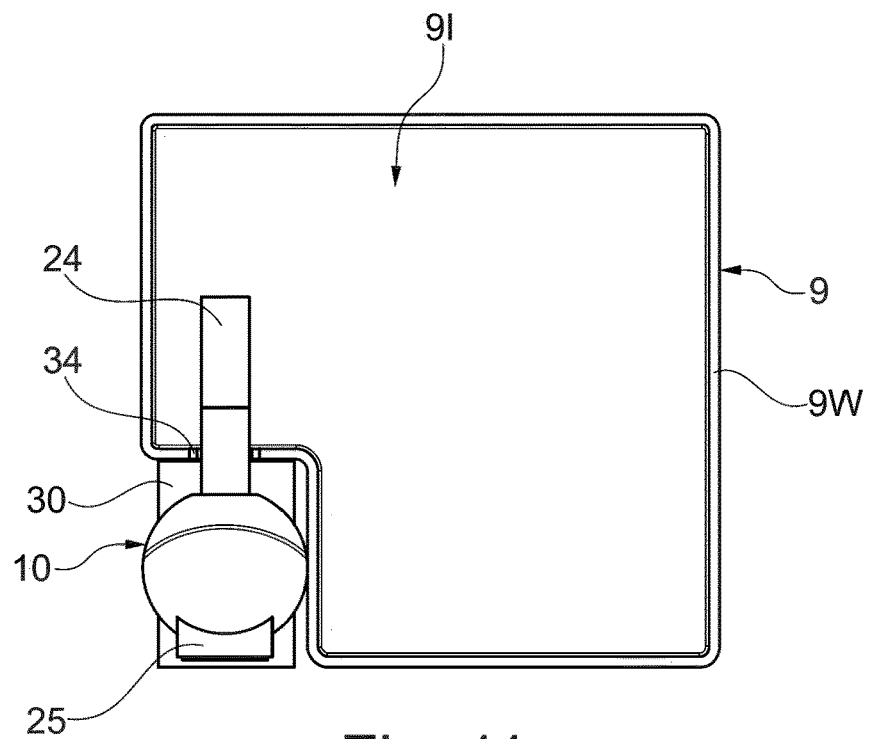
FIG. 11 is a top view of the housing base with the vision device positioned on the receptacle of the housing base.
Figure 12:
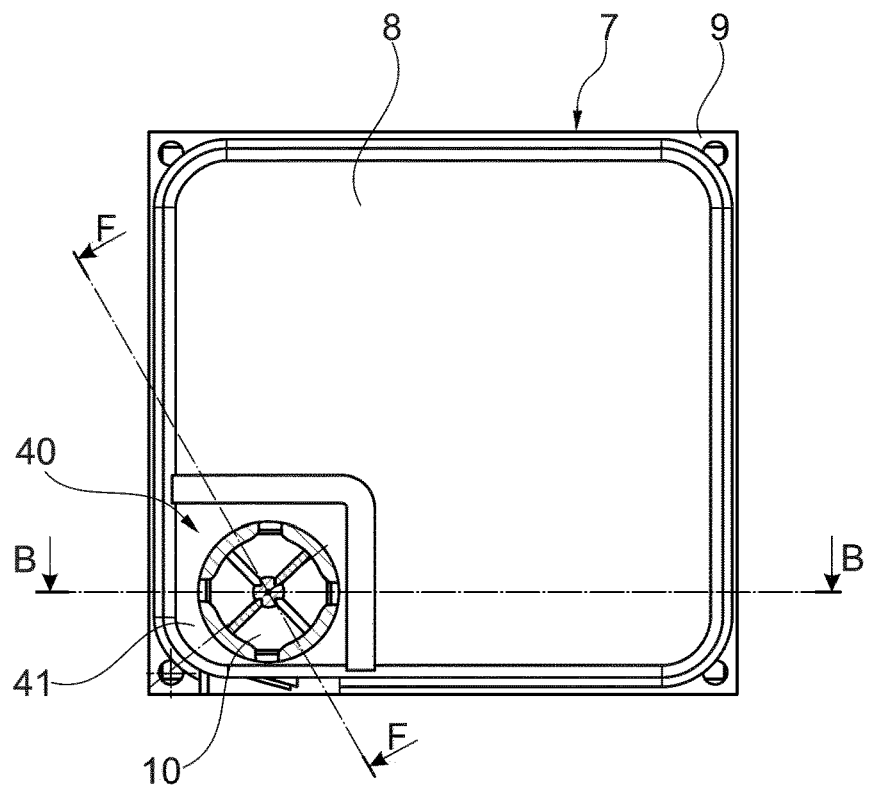
FIG. 12 is a top view of one embodiment of the housing cover mounted to the housing base according to a first embodiment.

A top view of the housing base 9 is shown in FIG. 11. The vision device 10 is positioned on the flange 30 of the receptacle 16 of housing base 9. The band cable 24 of the vision device 10 is guided through the passage 34 of surrounding wall 9W of housing base 9 into the inner portion 9I of housing base 9. Housing base 9 accommodates a printed circuit board (not shown here) to which the band cable 24 is connected. The inner portion 9I of housing base 9 is separated from the at least one vision device 10 by surrounding wall 9W. Neck 25 of vision device 10 is pointing to the outside of housing base 9.

Figure 14:
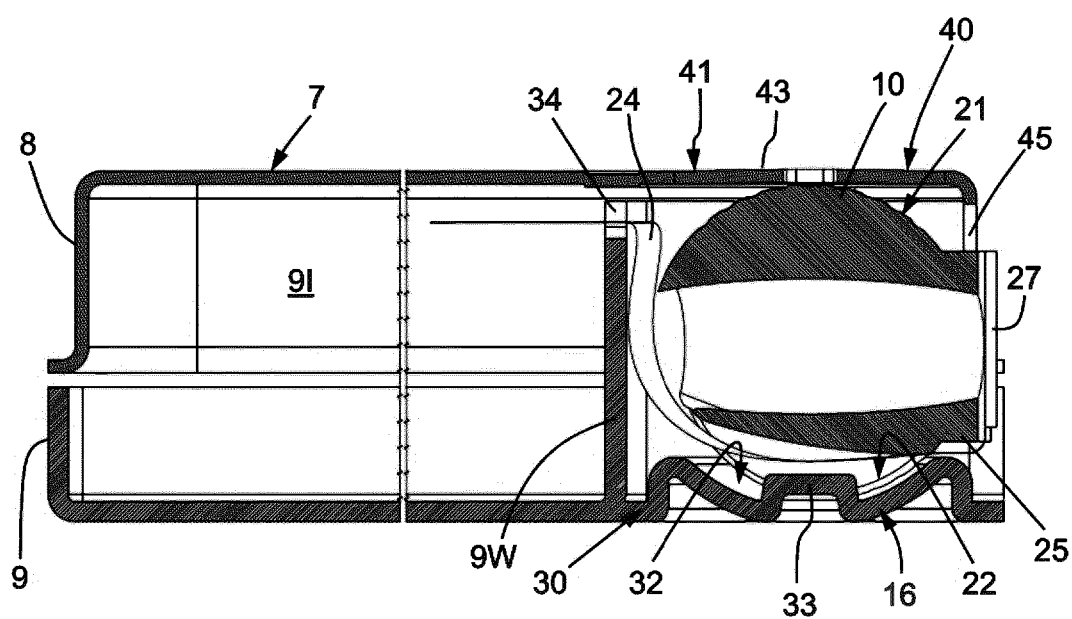
FIG. 14 is an enlarged sectional view of the outer housing along line A-A in FIG. 13 prior to the joining on the housing cover and the housing base.

FIGS. 12 to 19 provide an insight of the mounting of the vision device 10 according to a first embodiment. The housing cover 8 is placed on top of the housing base 9 and thereby mounts the at least one vision device 10 therebetween. The housing cover 8 has a formed on mounting element 40 which is a flexible flange 41 in the present embodiment. The flexible flange 41 has an area 43 with a topology 42 (see FIG. 14, FIG. 17, FIG. 19) that mates the first spherical outer contour 21 of the vision device 10 when the housing cover 8 and the housing base 9 are mounted and form the outer housing 7. FIG. 14 shows the situation in which the housing cover 8 and the housing base 9 are still separated a bit from each other and are not yet mounted together. The vision device 10 rests with its second spherical outer contour 22 on the spherical portion 32 of the receptacle 16 of flange 30. The central pin 33 is used to center the vision device 10 on the receptacle 16 and limits the rotational movement of the vision device 10 on the receptacle 16. The neck 25 of the vision device 10 is pointing through a window 45 of the outer housing 7. The flexible area 43 of flange 41 of the housing cover 8 is touching the first spherical outer contour 21 of the housing 20 of the vision device 10. The band cable 24 is guided from the flexible printed circuit board 27 to the inner portion 9I of the outer housing 7.

Figure 15:
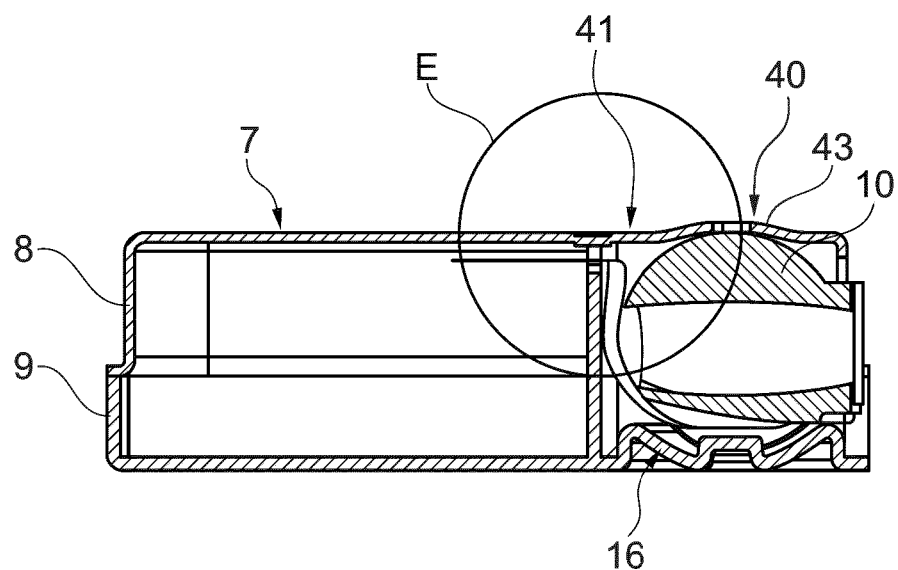
FIG. 15 is a sectional view of the outer housing along line A-A in FIG. 13, wherein the housing cover and the housing base are joined.
Figure 16:
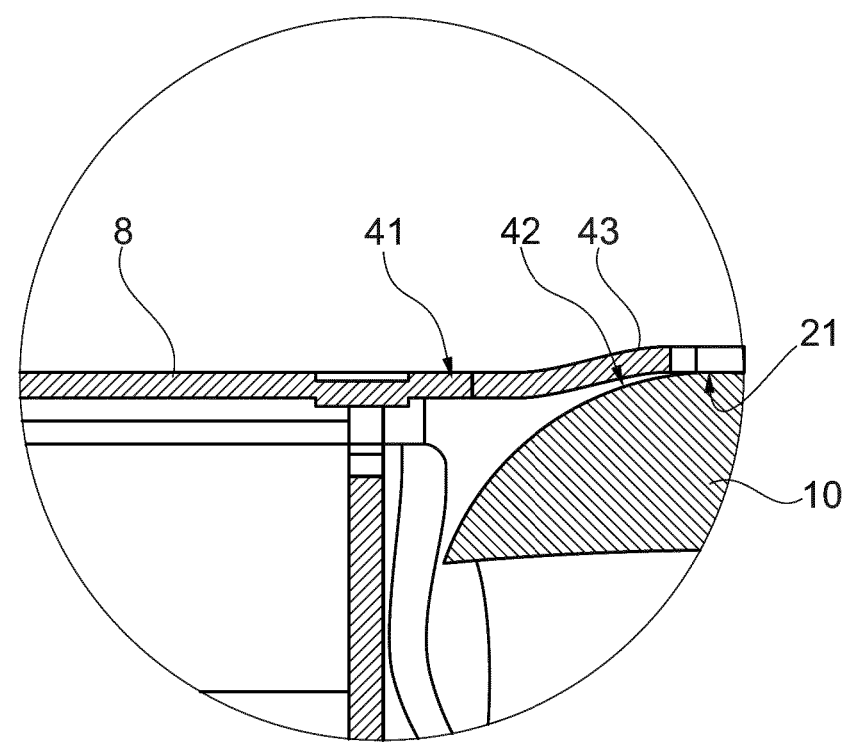
FIG. 16 is an enlarged view of the area of the outer housing marked with the circle E in FIG. 15.
Figure 17:
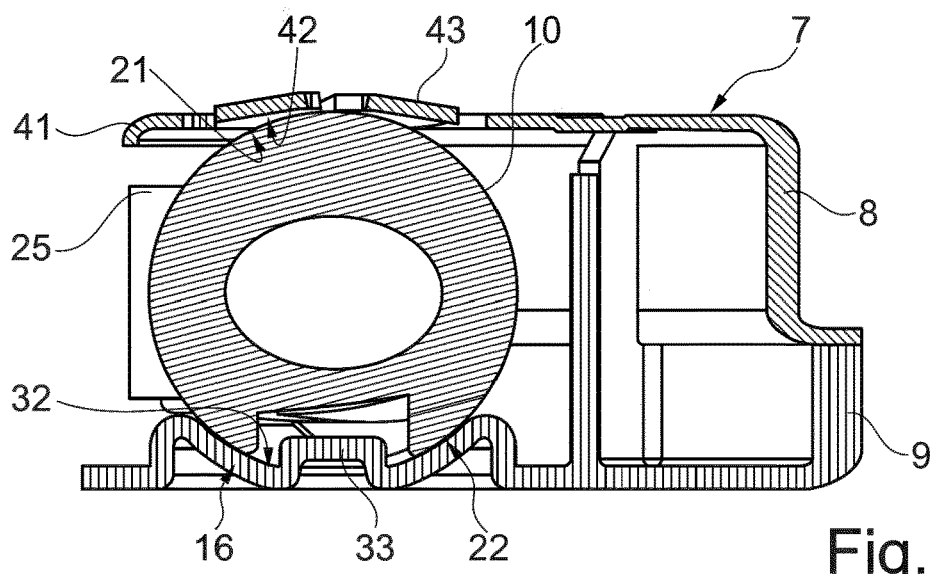
FIG. 17 is an enlarged, sectional view along line F-F in FIG. 12, wherein the vision device is mounted in the outer housing.
Figure 18:
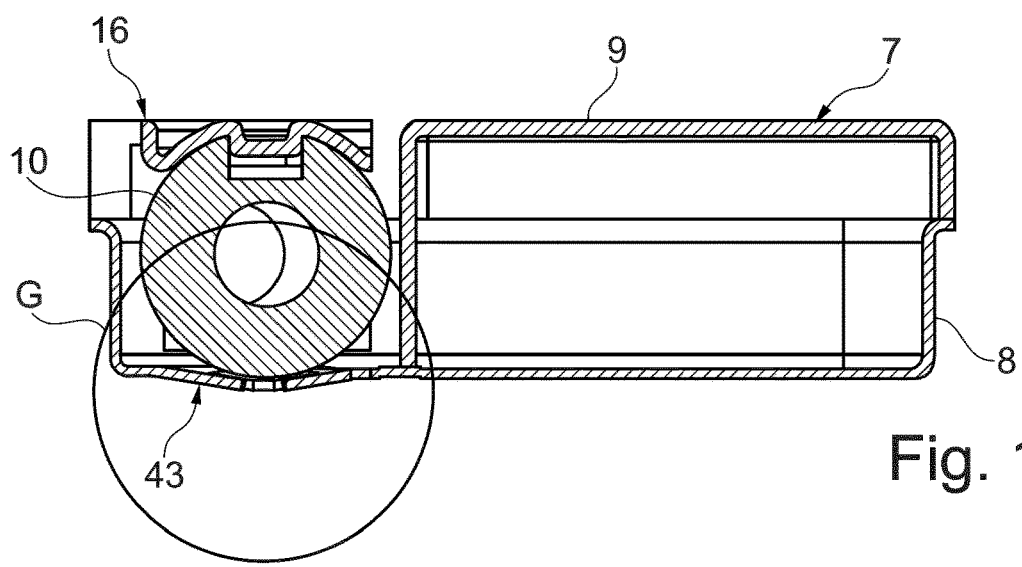
FIG. 18 is an enlarged sectional view of the outer housing along line B-B in FIG. 12.
Figure 19:
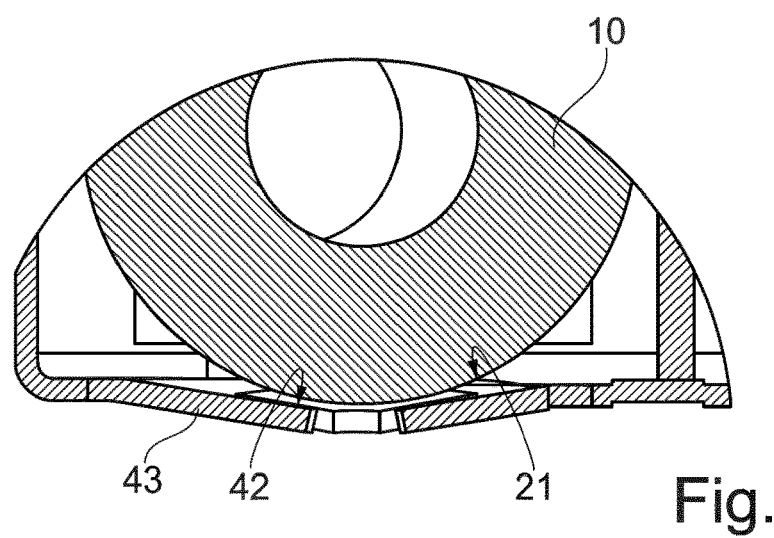
FIG. 19 is an enlarged view of the area of the outer housing marked with the circle Gin FIG. 18.

In FIGS. 15 and 16, the mounting situation of the housing cover 8 and the housing base 9 is shown. Here, the housing cover 8 and the housing base 9 are joined together and thus form the outer housing 7. FIG. 16 is the enlarged view of the area E in FIG. 15 which is a sectional view along line A-A in FIG. 13.

When the housing cover 8 and the housing base 9 are joined together, the topology 42 of the area 43 of the flexible flange 41 mates the first spherical outer contour 21 of the vision device 10. The flexible flange 41 provides an appropriate tension so that the second spherical outer contour 22 of vision device 10 is in contact with the spherical portion 32 of the receptacle 16.

The mounting of the outer housing 7 is carried out in several steps. The main printed circuit board (not shown) is mounted inside the housing base 9. As shown in FIGS. 12 to 19, the vision device 10 is seated on the receptacle 16 of the housing base 9. Optionally, a minimal force may be exerted on the vision device 10 via a gripper (not shown), so that the vision device 10 does not move during the following mounting step or steps. The vision device 10, sitting on the receptacle 16, can oriented to an angular position as required by the type of vehicle 2 in which the driver monitoring system 1 is used. Then the housing cover 8 is lowered down unto the housing base 9. As the housing cover 8 begins the descent, the cover flange 41 of the housing cover 8 first contacts the first spherical outer contour 21 of the vision device 10. The clamping force, exerted onto the vision device 10, increases up to a maximum value when the housing cover 8 and the housing base 9 are fully joined. The housing cover 8 and the housing base 9 are fixed together by conventional means, for example screws. Finally, the optional gripper is disengaged.

Figure 20:
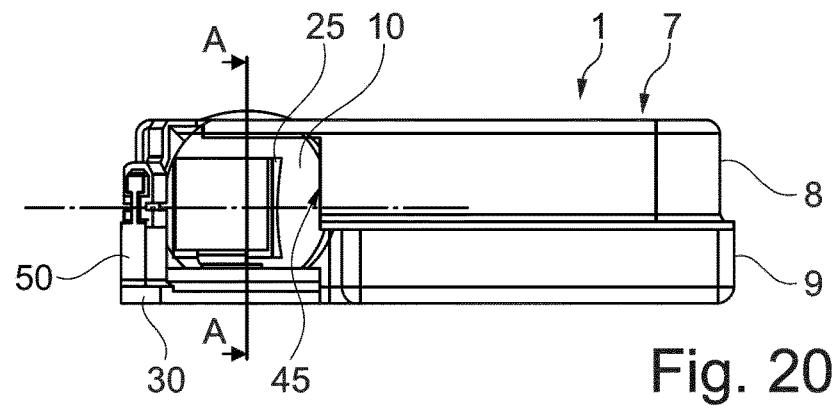
FIG. 20 is a side view of an additional embodiment of the driver monitoring system, wherein the vision device is mounted between the housing base and the housing cover.
Figure 21:
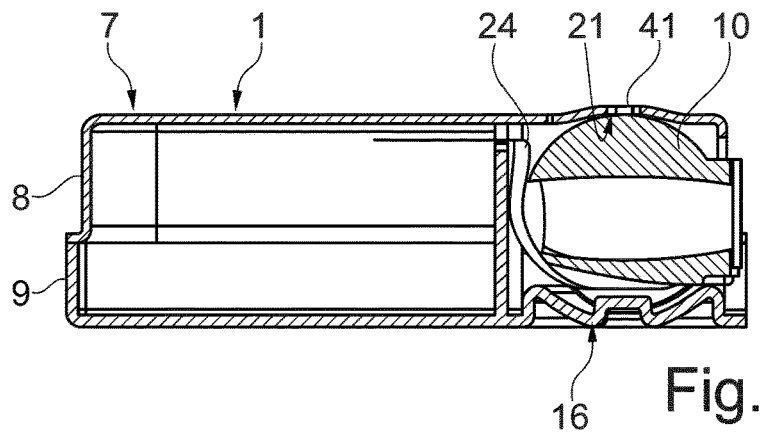
FIG. 21 is an enlarged sectional view of the outer housing along line A-A in FIG. 20 of the joined housing cover and housing base.

FIGS. 20 to 28 provide an insight to the mounting of the vision device 10 according to a further embodiment. The driver monitoring system 1 has the vision device 10 mounted as well between the housing base 9 and the housing cover 8. As shown in FIG. 20, the vision device 10 is held in the outer housing 7 so that the neck 25 of the vision device 10 points to the outside of the housing. A sectional view along line A-A in FIG. 20 is shown in FIG. 21. The vision device 10 is seated on the receptacle 16 of the housing base 9 (already described in detail in FIGS. 14 and 17). When the housing cover 8 and the housing base 9 are cojoined, the mounting element 40 is in form and force fit contact with the first spherical outer contour 21 of the vision device 10.

A clinching dome 50 (see FIG. 20) is provided at the flange 30 of the housing base 9. As shown by the top view of the outer housing 7 in FIG. 22, the flexible area 43 of the flexible flange 41 is connected to the clinching dome 50. As a result, the flexible area 43 is in contact with the first spherical outer contour 21 of the vision device 10.

Figure 22:
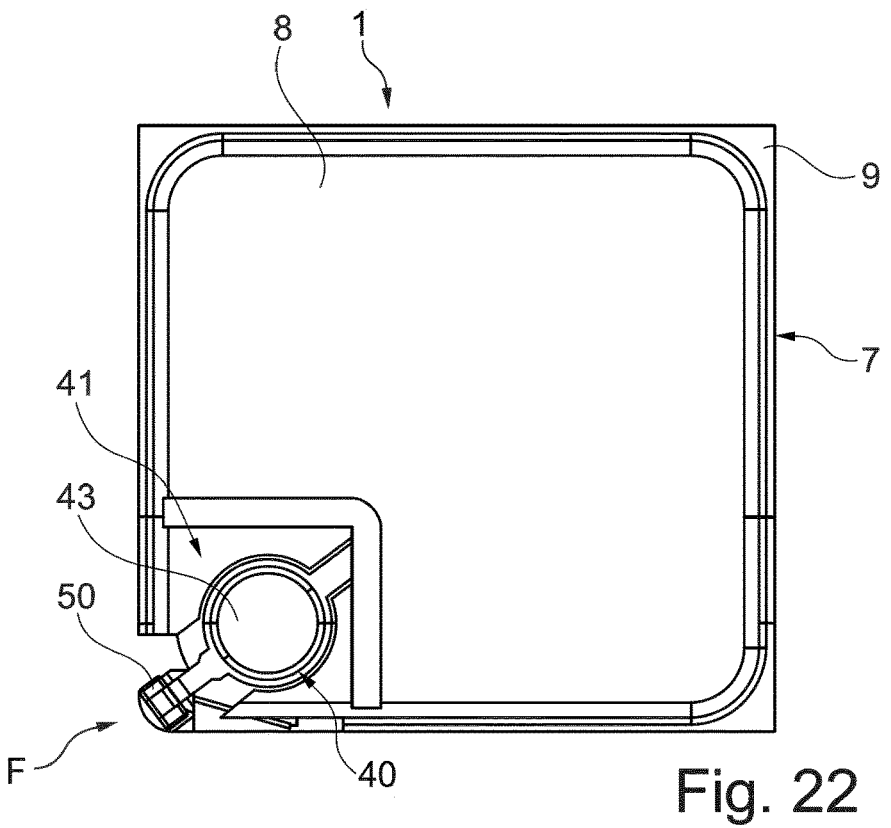
FIG. 22 is a top view of the housing cover mounted to the housing base of the embodiment in FIG. 20.
Figure 23:
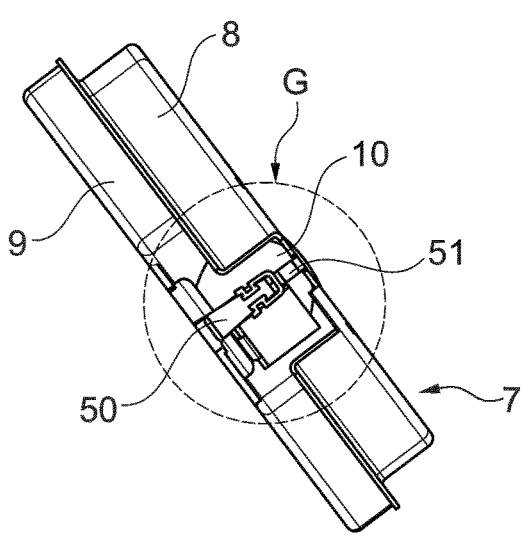
FIG. 23 shows a view of the driver monitoring system along the viewing direction F (see FIG. 22) of the joined housing cover and housing base.
Figure 24:
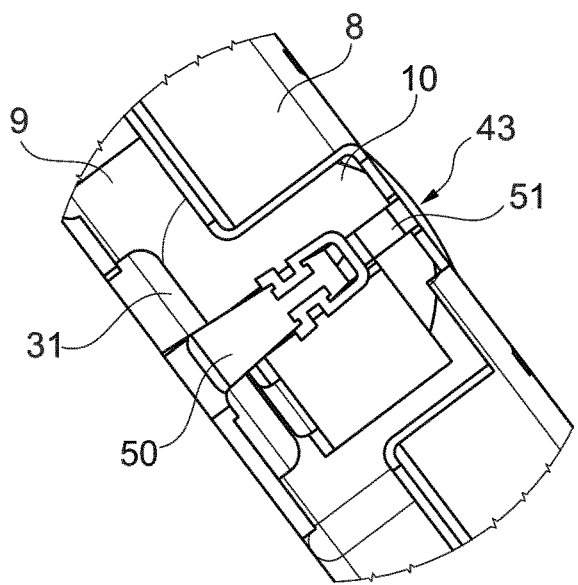
FIG. 24 is an enlarged view of the area G as shown in FIG. 23.

FIG. 23 is a side view of the driver monitoring system 1 from the direction F as shown in FIG. 22, and FIG. 24 is an enlarged view of the area marked with G in FIG. 23. The clinching dome 50 is in a form fit contact with an elongation 51 of the flexible area 43 once the housing base 9 and the housing cover 8 are conjoined. Due to the joined clinching dome 50, the elongation 51 of the flexible area 43 exerts a force onto the vision device 10. Consequently, the vision device 10 is held in position by the flexible area 43 and the siting surface 31.

Figure 25:
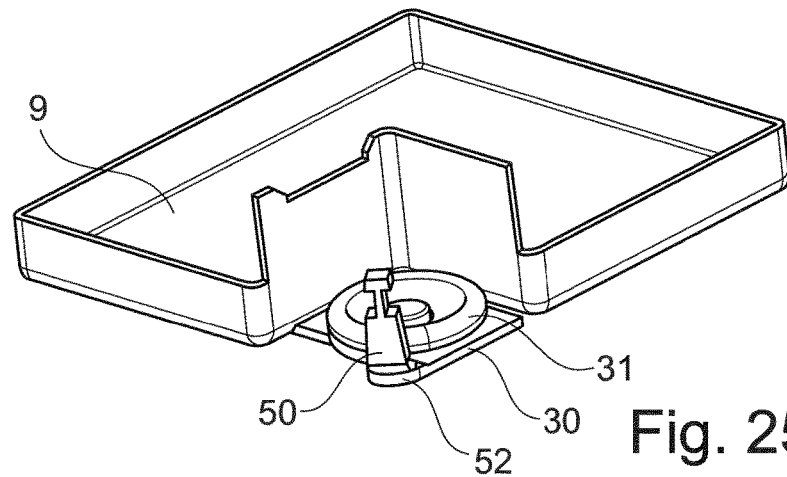
FIG. 25 is a perspective view of the housing base with the clinching dome.

FIG. 25 shows a perspective view of the housing base 9 with the clinching dome placed in a corner 52 of the flange 30, which carries the siting surface 31. The height and width of the clinching dome 50 can be adjusted to the required needs.

Figure 26:
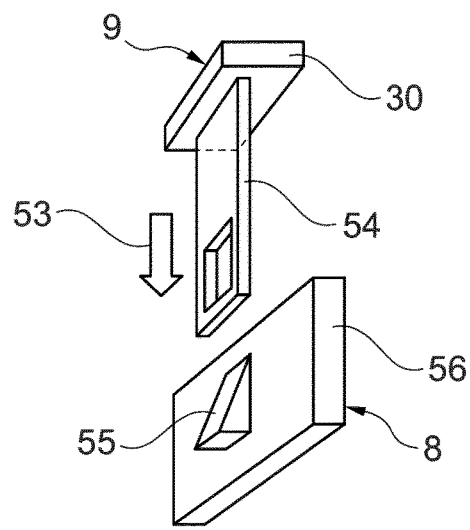
FIG. 26 is a detailed view of an embodiment of the elastic snap feature for joining the housing cover and the housing base.

FIG. 26 shows a further embodiment for a mechanism connecting the housing cover 8 to the housing base 9. A lug topology 54 is formed, for example, on the corner 52 (see FIG. 25) of the flange 30 of the housing base 9. On the housing cover 8, a hook 55 will be located onto a snapping dome 56. Along direction 53, the lug topology 54 and the snapping dome 56 are moved towards each other. Once the lug topology 54 and the snapping dome 56 cooperate, the housing cover 8 and the housing base 9 are conjoined.

Figure 27:
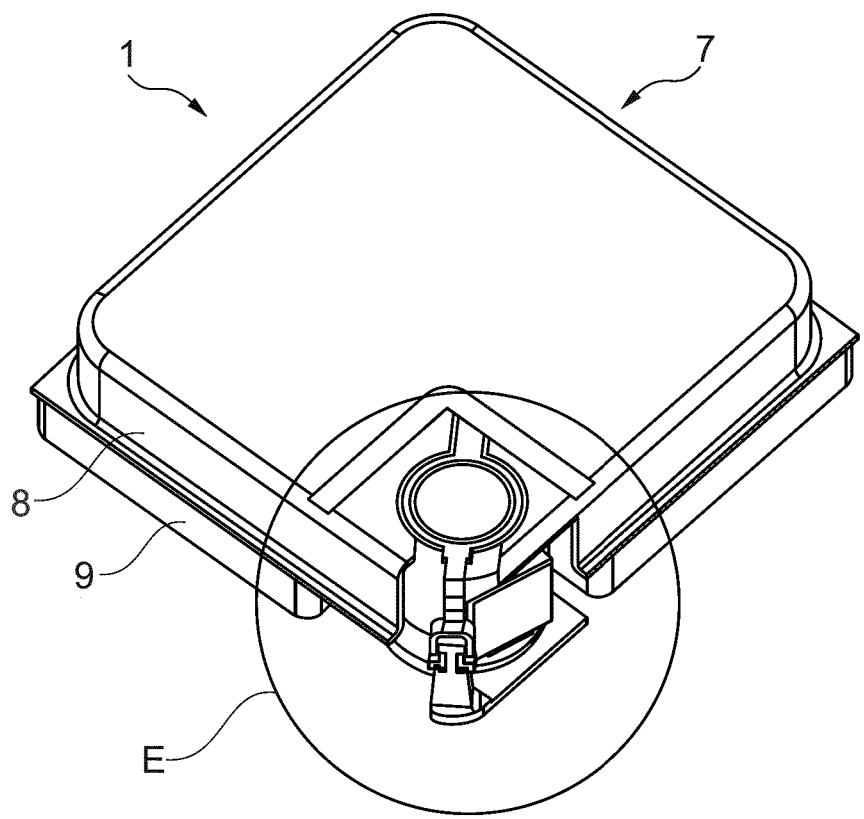
FIG. 27 is a perspective top view of the mounted housing base and housing cover which are joined together by clinching.
Figure 28:
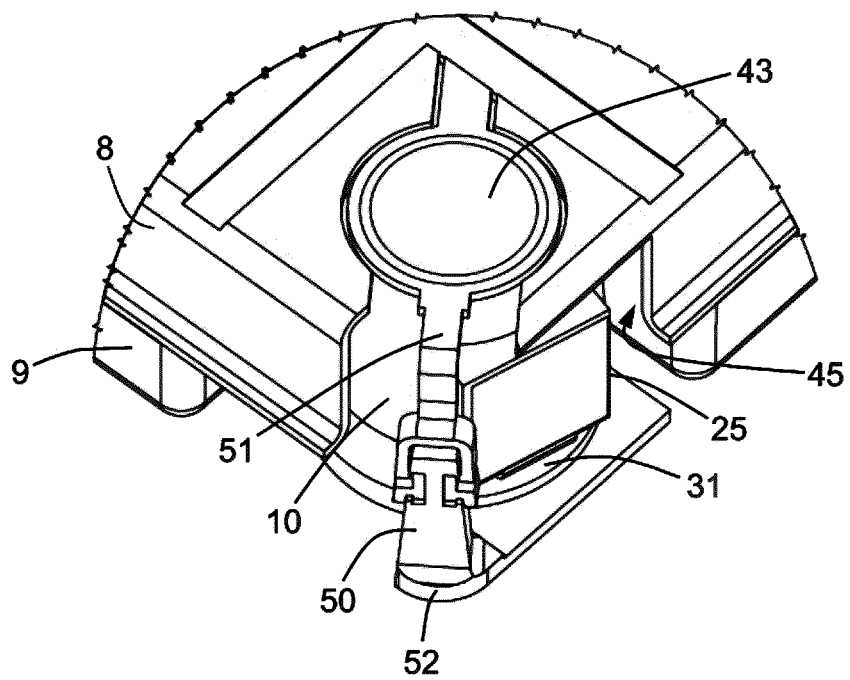
FIG. 28 is an enlarged view of the area marked E in FIG. 27.

FIG. 27 shows a perspective view of the outer housing 7 of the driver monitoring system 1, and FIG. 28 shows an enlarged view of the area marked with E in FIG. 27. The housing cover 8 and the housing base 9 are conjoined and form the outer housing 7. The clinching dome 50 and the elongation 51 are connected and fix the vision device 10 in the outer housing 7. The vision device 10 is positioned between the siting surface 31 and the flexible area 43. The neck 25 of the vision device 10 points through the window 45.

Figure 29:
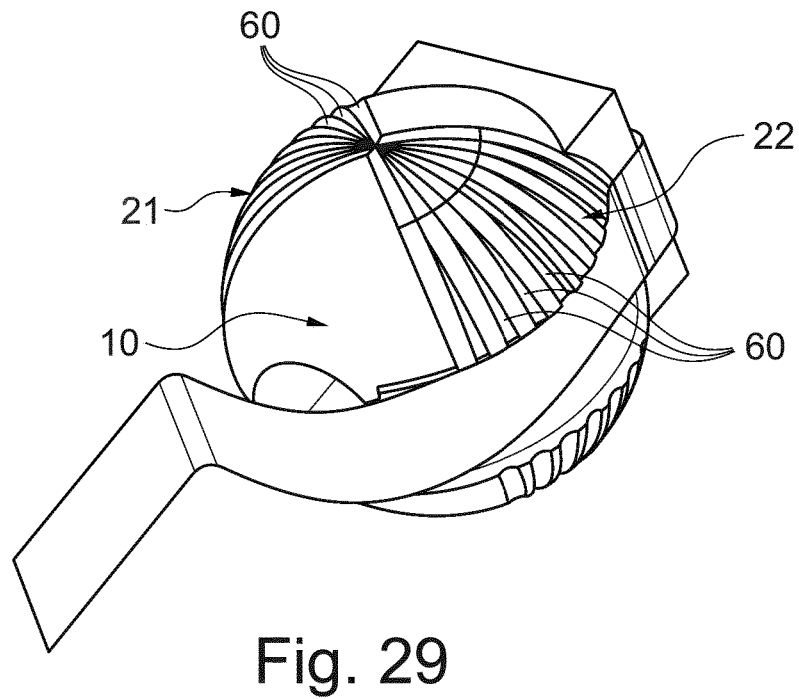
FIG. 29 is a perspective view of a further embodiment of the vision device.
Figure 30:
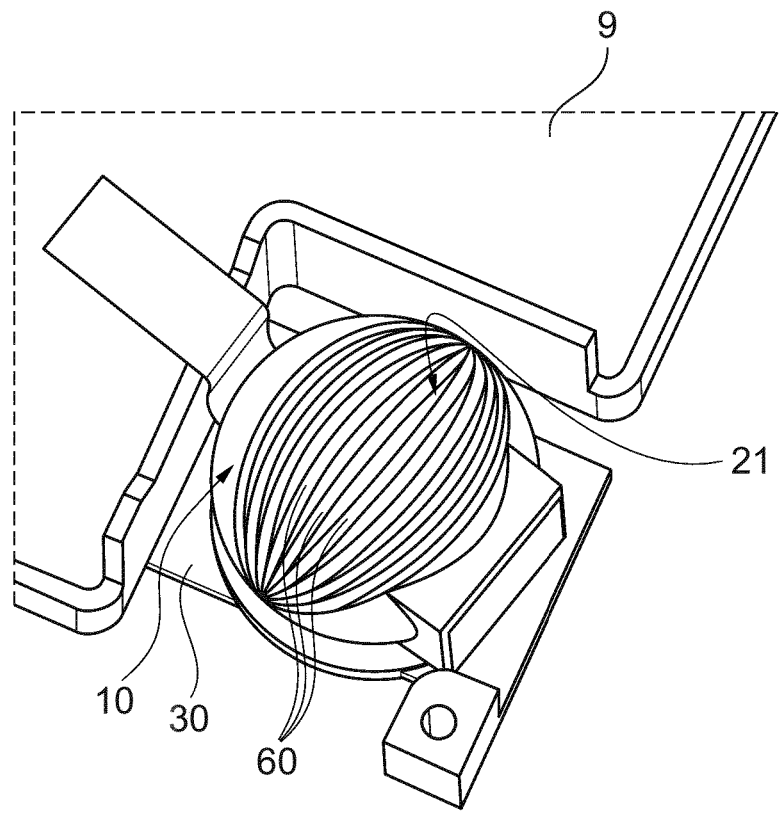
FIG. 30 is a perspective top view of the embodiment of the vision device of FIG. 29 placed on the housing base.

FIG. 29 is a perspective view of a further embodiment of the vision device 10. FIG. 30 is a perspective top view of the embodiment of the vision device 10 of FIG. 29 placed on the flange 30 of housing base 9. The vision device 10 has an array of shallow grooves 60 formed at least on the first spherical outer contour 21 and the second spherical outer contour 22 of the vision device 10. The shallow grooves 60 provide an additional support for the position fixation of the vision device 10.

Figure 31:
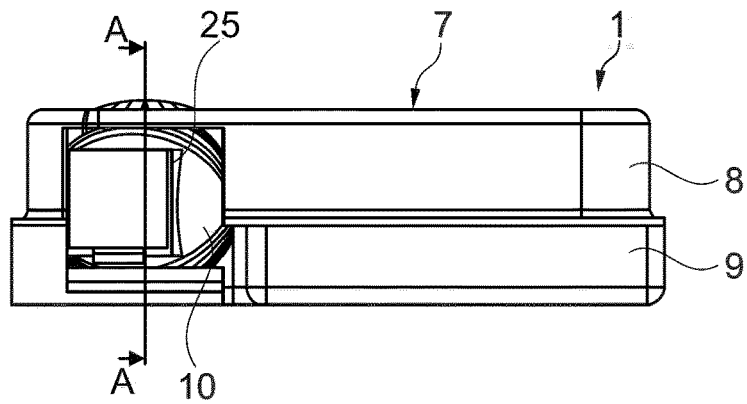
FIG. 31 is a side view of an additional embodiment of the driver monitoring system, wherein the vision device is mounted between the housing base and the housing cover.
Figure 32:
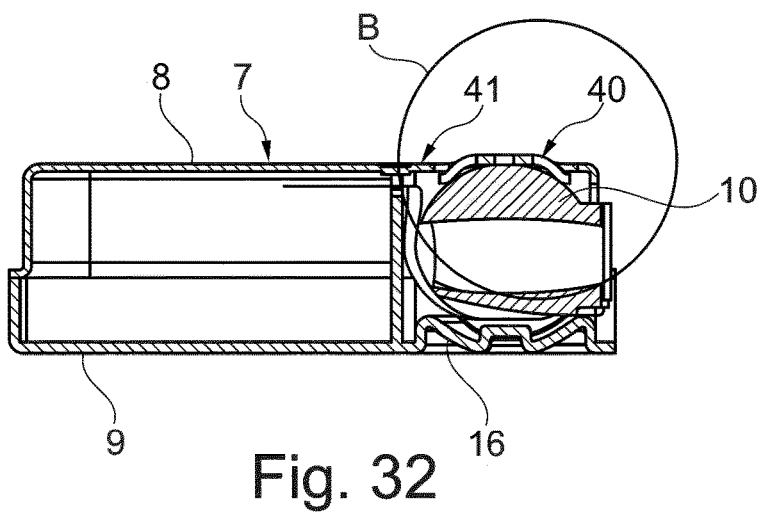
FIG. 32 is a sectional view of the outer housing along line A-A in FIG. 31, wherein the housing cover and the housing base are joined.

FIGS. 31 to 35 show an embodiment of mounting the embodiment of the vision device 10 shown in FIGS. 29 and 30. The driver monitoring system 1 comprises the vision device 10 mounted as well between the housing base 9 and the housing cover 8. As shown in FIG. 31, the vision device 10 is held in the outer housing 7, so that neck 25 of vision device 10 points to the outside of outer housing 7. A sectional view along line A-A in FIG. 31 is shown in FIG. 32. The vision device 10 is seated on the receptacle 16 of the housing base 9 (already described in detail in FIGS. 14 and 17). The mounting element 40 of the flange 41 of the housing cover 8 is in contact with the first spherical outer contour 21 of the vision device 10. The housing cover 8 and the housing base 9 are cojoined. The mounting of the housing cover 8 to the housing base 9 can be carried out, for example, by screws (not shown).

Figure 33:
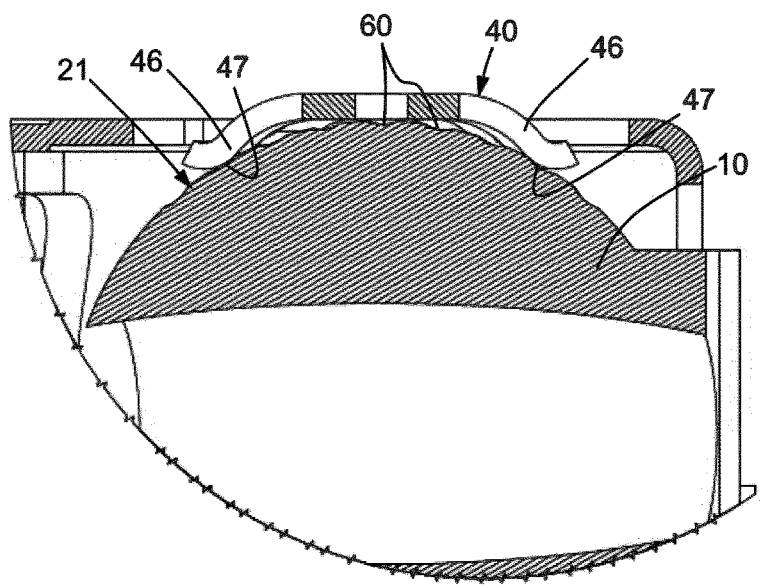
FIG. 33 is an enlarged view of the embodiment shown in FIG. 32 and marked with B.

FIG. 33 is an enlarged, sectional view of the area marked with B in the embodiment shown in FIG. 32. The vision device 10 has an array of shallow grooves 60 formed at least on the first spherical outer contour 21 of vision device 10. In an embodiment shown here, the mounting element 40 has a plurality of flexible fingers 46. A tip portion 47 of the flexible fingers 46 is in form and force fitting contact with the respective shallow groove 60 when the housing cover 8 is fully joined with the housing base 9.

Figure 34:
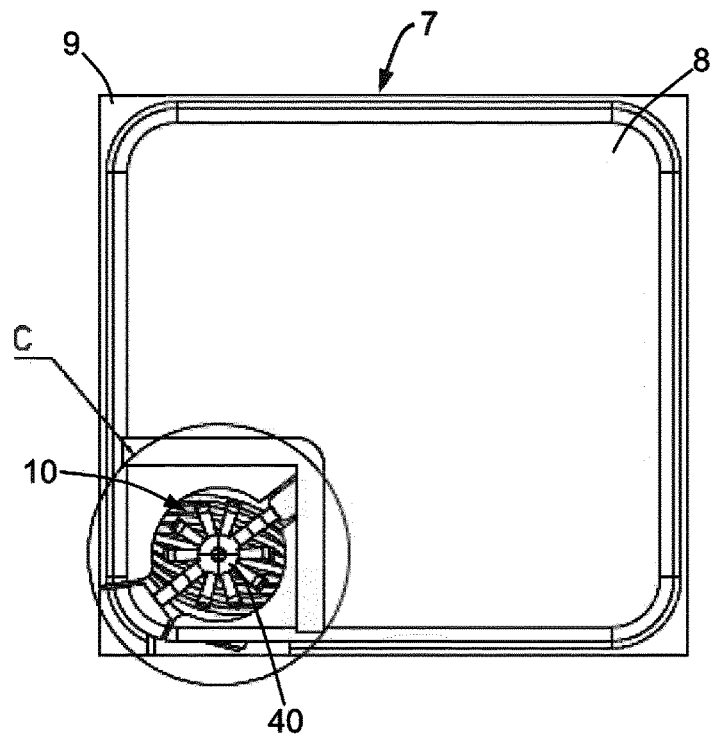
FIG. 34 is a top view of a further embodiment of the mounting of the vision device in the outer housing.
Figure 35:
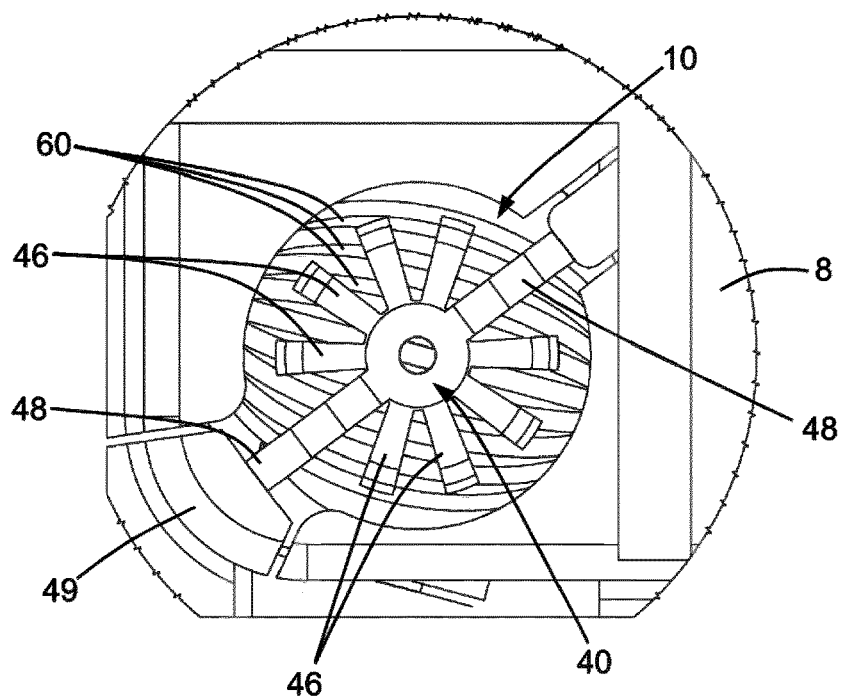
FIG. 35 is an enlarged view of the area marked with C in FIG. 34.

FIG. 34 shows a top view of the joined housing cover 8 and housing base 9, forming the outer housing 7 of the driver monitoring system 1. In an embodiment shown here, the housing cover 8 carries the mounting element 40 which interacts with the vision device 10. FIG. 35 is an enlarged view of the area marked C in FIG. 34. The embodiment of the mounting element 40 shown here has a circular array of flexible fingers 46 which are symmetrically arranged at the mounting element 40. As the housing cover 8 is fully lowered on the housing base 9 (see FIG. 34), the spring effect of the flexible fingers 46 reaches a maximum and the tip portion 47 of the flexible fingers 46 are in contact with respective shallow grooves 60 on the first spherical outer contour 21 of the vision device 10. The advantage of the shallow grooves 60 is that an anti-rotation effect of the vision device 10 is improved when the tip portion 47 of the flexible fingers 46 interact with respective shallow grooves 60. The mounting element 40 is attached via a flexible strip 48 to the housing cover 8. Opposite to the attachment of the flexible strip 48 to the housing cover 8, the flexible strip 48 is attached to a fixing 49 which can be attached to the housing base 9. In addition, a screw (not shown) may clamp even more the fixing 49 and consequently the vision device 10 when the housing cover 8 and the housing base 9 are fully joined.

Figure 36A:
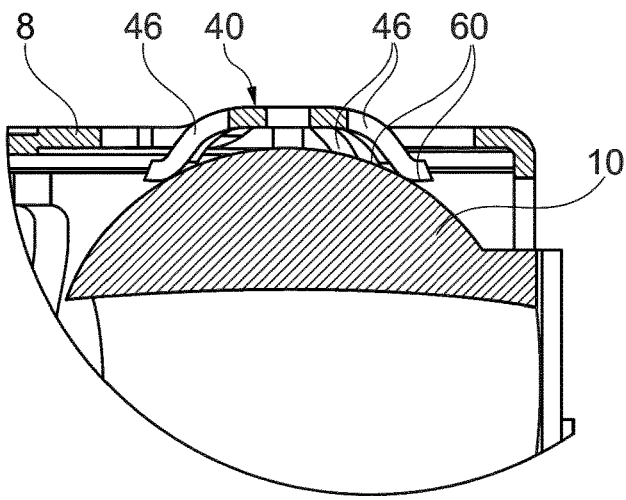
FIGS. 36A and 36B are detailed views of the finger flanges, contacting the vision device during the mounting process.
Figure 36B:
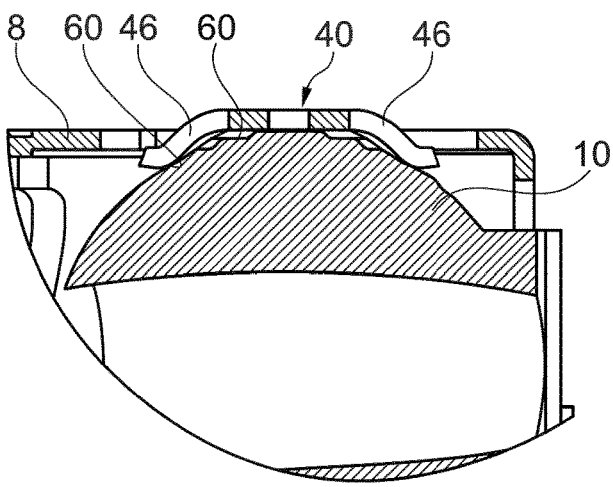

FIGS. 36A and 36B show a detailed view of the flexible fingers 46, contacting the vision device 10 during the mounting process. The tip portion 47 of the flexible fingers 46 are the first to get in contact with the first spherical outer contour 21 of the vision device 10, when the housing cover 8 is lowered down onto the housing base 9 (see FIG. 36A). When the housing cover 8 is fully lowered on the housing base 9, the spring effect of the flexible fingers 46 of the mounting element 40 enables a form and force fitting contact with the shallow grooves 60 on first spherical outer contour 21 of the vision device 10.

Figure 37:
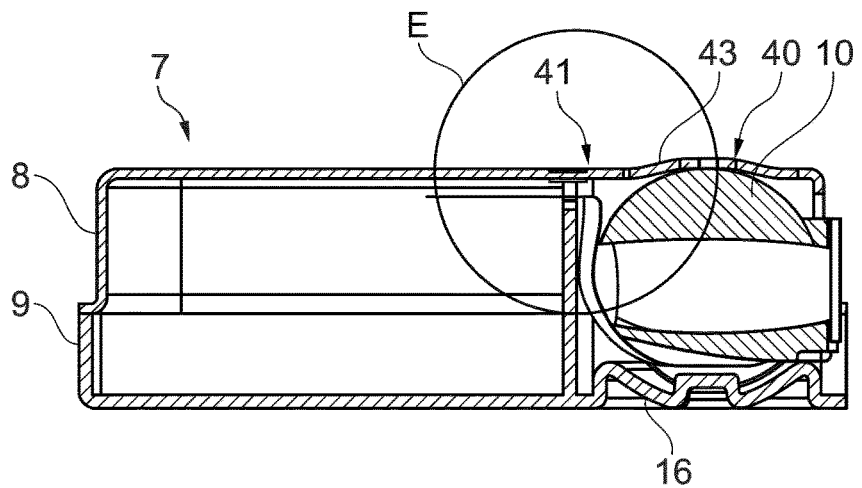
FIG. 37 is a sectional view of the outer housing, wherein the housing cover and the housing base are joined.

FIG. 37 is a sectional view of the outer housing 7, wherein the housing cover 8 and the housing base 9 are joined. The outer housing 7 is formed by the housing cover 8 joined with the housing base 9. The vision device 10 is arranged between the receptacle 16 and a flexible area 43 of the mounting element 40 being part of the flange 41.

Figure 38:
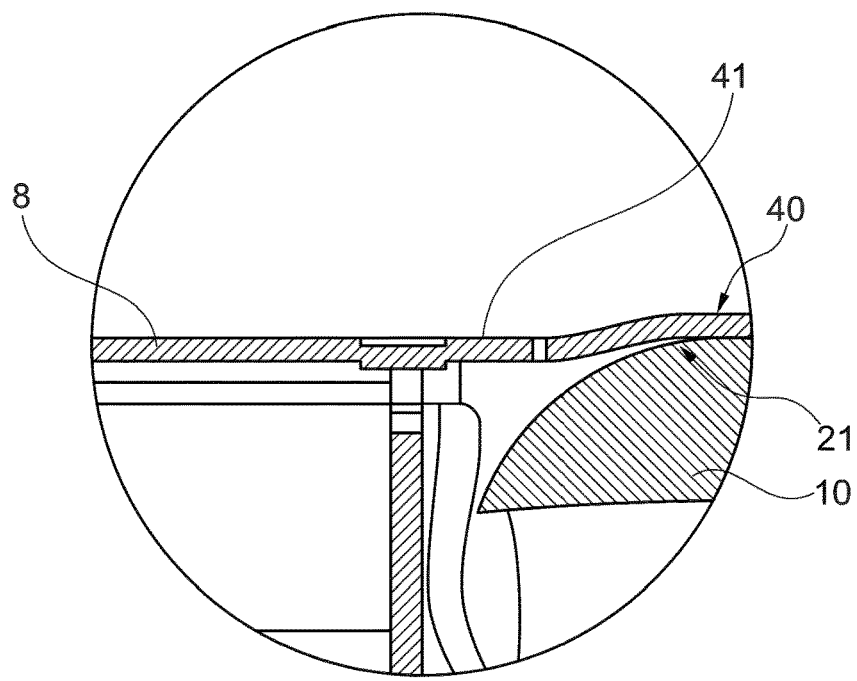
FIG. 38 is an enlarged view of the embodiment shown in FIG. 36 and marked with E.

FIG. 38 is an enlarged view of the area E in FIG. 37. The mounting element 40 is in close contact with the first spherical outer contour 21 of the vision device 10. The mounting element 40 is a part of the flange 41 of the housing cover 8.

Figure 39:
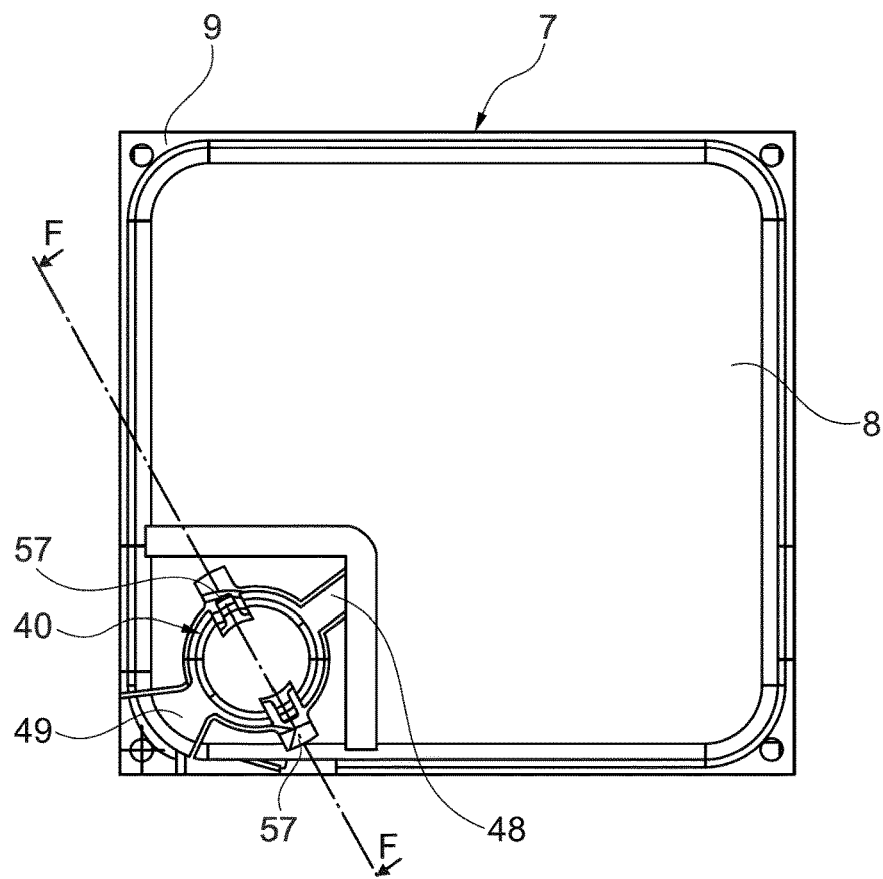
FIG. 39 is a top view of the housing cover, which has claw flanges for mounting the vision device.

FIG. 39 is a top view of the housing cover 8 mounted to the housing base 9. The mounting element 40 of the housing cover 8 has claw flanges 57 for mounting the vision device 10. With the flexible strip 48, the mounting element 40 is attached to the housing cover 8. The fixing 49 is attached to the housing base 9.

Figure 40:
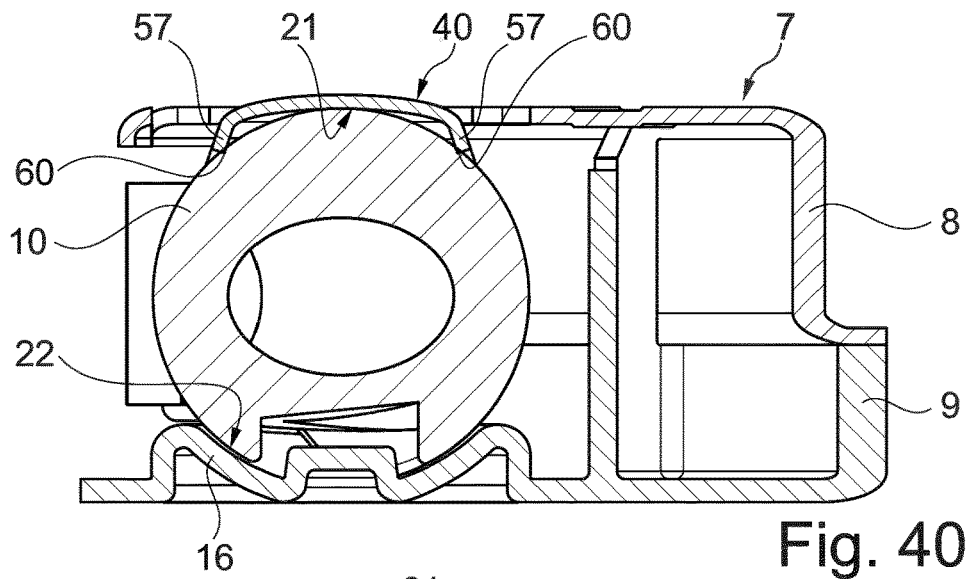
FIG. 40 is a sectional view of the outer housing along line F-F in FIG. 39, wherein the claw flanges are in contact with the vision device.

FIG. 40 is a sectional view of the outer housing 7 along line F-F in FIG. 39, wherein the claw flanges 57 are in contact with the first spherical outer contour 21 of the vision device 10. In the embodiment shown here, the claw flanges 57 are at least in form fitting contact with the grooves 60 of the first spherical outer contour 21 of the vision device 10. The housing cover 8 and the housing base 9 are joined, and the second spherical outer contour 22 of the housing device 10 is in form fitting contact with the receptacle 16.

Figure 41:
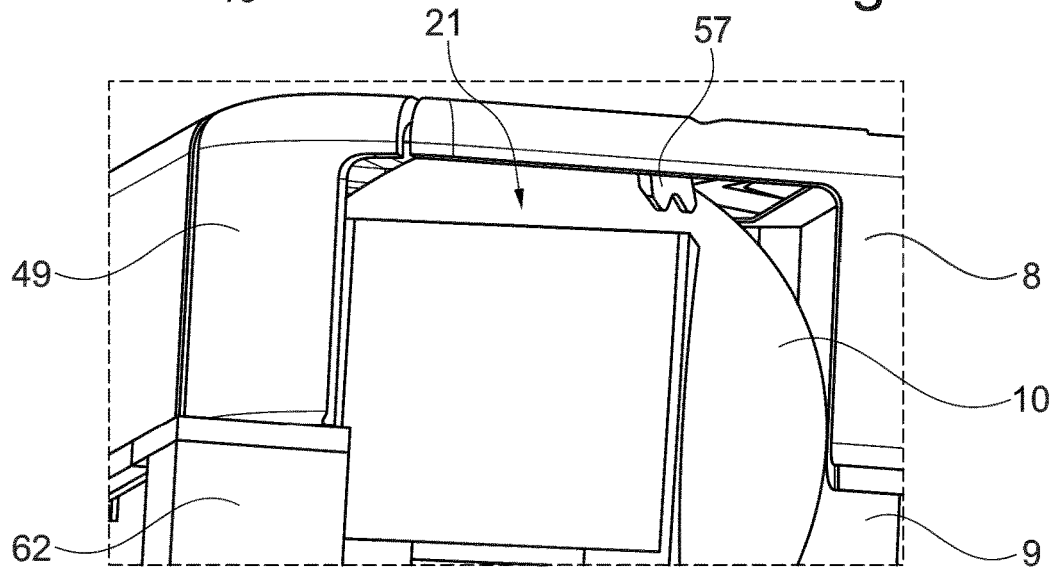
FIG. 41 is a detailed perspective view of the cooperation of the claw flanges with the vision device.
Figure 42:
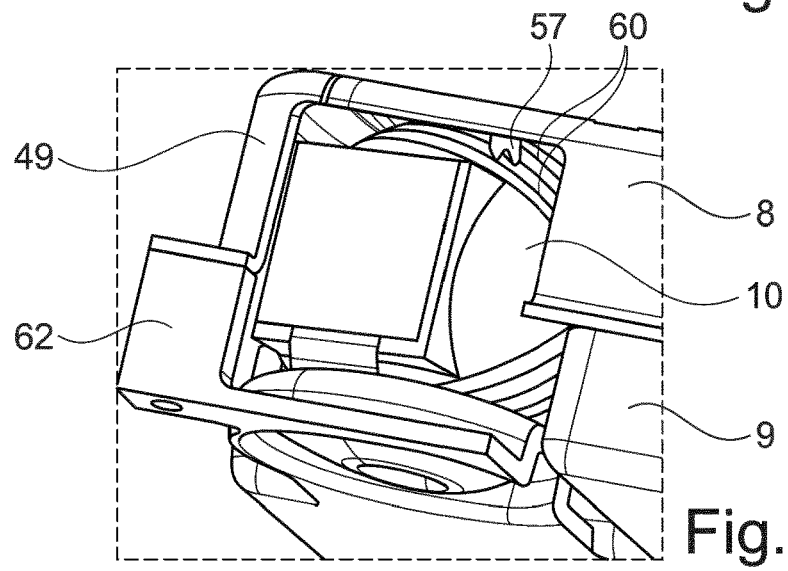
FIG. 42 is a detailed perspective view of the cooperation of the claw flanges with the embodiment of the vison device as shown in FIG. 39.

FIGS. 41 and 42 are detailed perspective views of the cooperation of the claw flanges 57 with the vision device 10. In the embodiment shown in FIG. 41, the claw flanges 57 cooperate with a smooth first spherical outer contour 21 of the vision device 10. The claw flanges 57, which are in contact with the first spherical outer contour 21 of the vision device 10, hinder the movement of the vision device 10 once the housing cover 8 and the housing base 9 are joined. FIG. 42 is a detailed perspective view of a further embodiment of the invention. The first spherical outer contour 21 of the vision device 10 has grooves and the claw flanges 57 are in at least in a form fitting contact with the grooves 60. It is apparent from FIGS. 41 and 42 that the housing cover 8 is joined with the housing base 9 by a screwing fixation of the fixing 49. Thereby, the housing cover 8 mounted to a screwing block 62 of the housing base 9. Once the fixing 49 of the mounting element 40 is attached to the screwing block 62 of the housing base 9, the claw flanges 57 will get as well into a force fitting contact with the first spherical outer contour 21 of the vision device 10. In the embodiment shown in FIG. 41, the first spherical outer contour 21 of the vision device 10 is a smooth surface. In the embodiment shown in FIG. 42 the first spherical outer contour 21 of the vision device 10 has a plurality of grooves 60. The claw flanges 57 will get into a form and force fitting contact with the first spherical outer contour 21 of the vision device 10. This embodiment requires partial or full release of the fixing 49 to the screwing block 62 so that the angular adjustment torque of the vision device 10 becomes as low as needed (for example, for hand adjustment and allowing orientation and reorientation with respect to the vision device 10).

Figure 43:
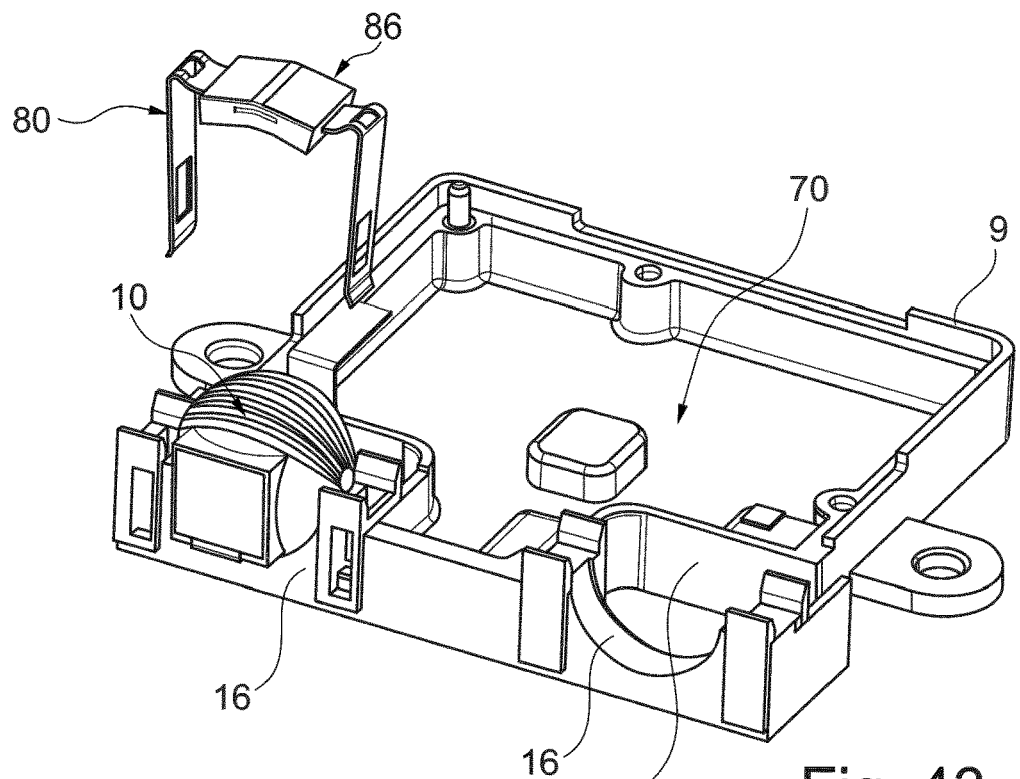
FIG. 43 is a perspective view of a further embodiment of mounting the vision device to the housing base.

FIG. 43 is a perspective view of the embodiment of the housing base 9 as shown in FIG. 4. The housing base 9 has two receptacles 16 for vision devices 10 (vision camera 11 and infrared module 12). The receptacle 16 may be fully placed, or only partially placed on the housing base 9. In the embodiment shown here the receptacle 16 is fully placed on the housing base 9. Generally, the receptacle 16 is separated from a main housing space 70 for a main printed circuit board (not shown) by walls that prevent dirt ingress into the main housing space 70. The vision devices 10 (vision camera 11 and infrared module 12 (infra-red projectors)) can withstand environmental challenges better than main printed circuit board.

As shown in FIG. 43 a vision device 10 is seated one of the receptacles 16 of the housing base 9. If required, the vision device 10 can be oriented to an angular position. Once the vision device 10 is oriented a hair pin spring 80 is used to fix the vision device 10 in the required orientation in the receptacle 16 of the housing base 9.

Figure 44:
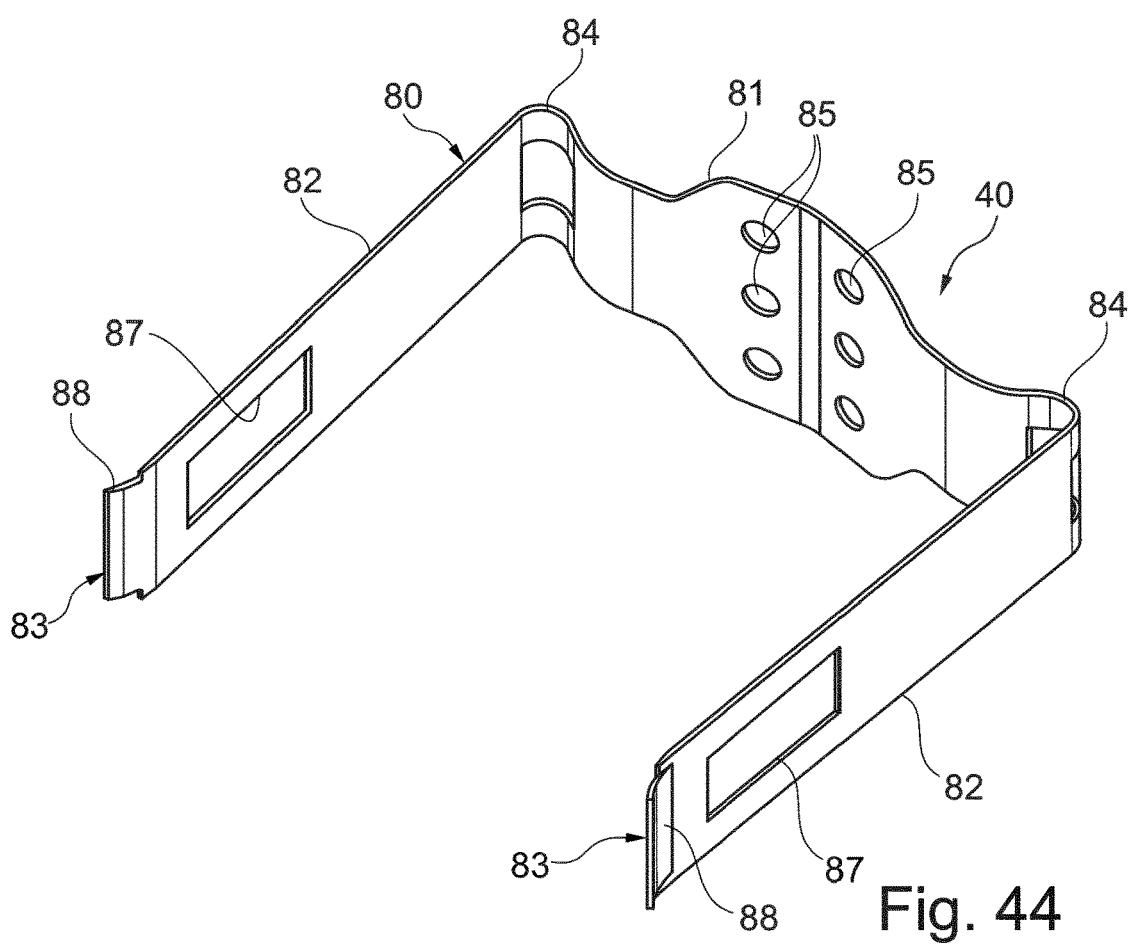
FIG. 44 is a perspective view of a hair pin spring for mounting the vision device.

FIG. 44 shows a perspective view an embodiment of a mounting element 40 which is a hair pin spring 80 for mounting the vision device 10 to the housing base. The hair pin spring 80 has a U-shaped form with a base 81 and two arms 82 extending from the base 81. Each arm 82 has a free end 83 and is connected via a shoulder 84 to the base 81. The base 81 has a plurality of holes 85, which are used to fix an overmolded part 86 (see FIG. 45) to the base 81 of the hair pin spring 80. Additionally, each arm 82 features a lug 87 which can engage with a mounting hook (see FIGS. 47 to 49) of the housing base 9. A pre-guide 88 is formed at the free 83 end of each arm 82.

Figure 45:
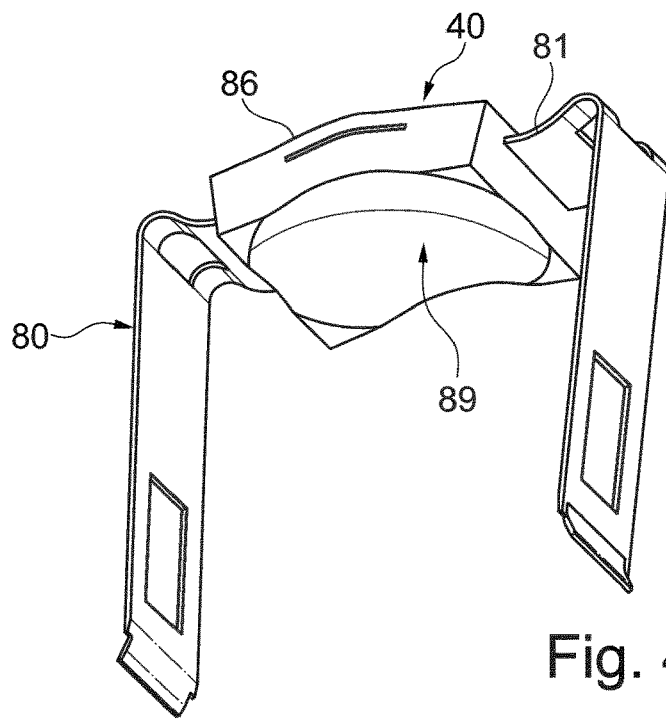
FIG. 45 is a perspective view from below of the hair pin spring, wherein the center of the hair pin spring is overmolded.

FIG. 45 is a perspective view of an embodiment of the hair pin spring 80. The base 81 of the hair pin spring 80 carries the overmolded part 86. The overmolded part 86 of the hair pin spring 80 provides an additional plastic zone. The overmolded part 86 has a spherical contact area 89 toward the vision device 10 (not shown here). With the spherical contact area 89 a clamping force is transferred from the hair pin spring 80 to the vision device 10. The spherical contact area 89 contact mainly the first spherical outer contour 21 of the vision device 10 and provides an anti-rotation friction after the assembly (preventing a change of the vision device 10 instalation angle).

Figure 46A:
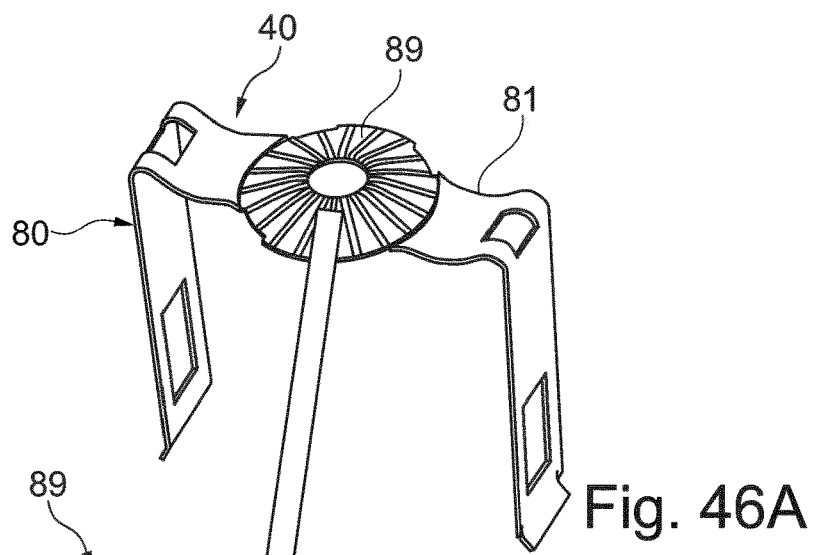
FIGS. 46A and 46B are perspective views of an embodiment of the hair pin spring with a spherical contact area for the vision device and a detailed view of the spherical contact area.
Figure 46B:
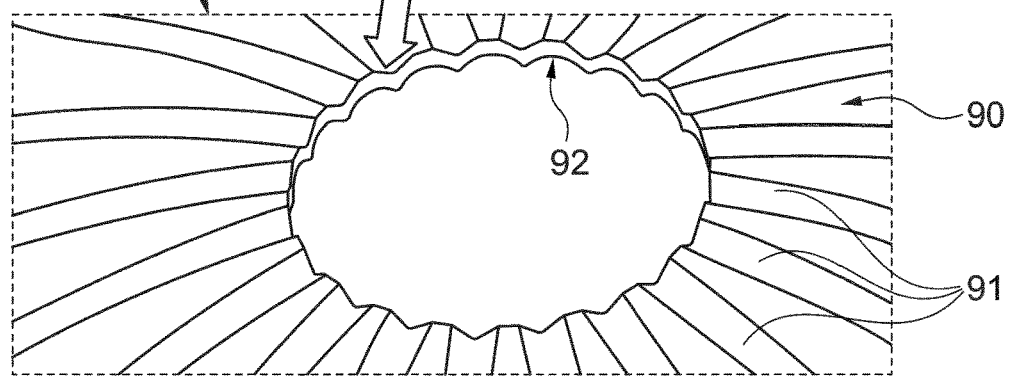

FIGS. 46A and 46B is perspective view of a further embodiment of the mounting element 40, which is a hair pin spring 80 with a spherical contact area 89 for the vision device 10, FIG. 46B is a detailed view of the spherical contact area 89. As shown in FIG. 46B the spherical contact area 89 has a formed topology 90 (ribs, dots, texture, etc.), creating by graining, which gets into contact with the first spherical outer contour 21 of the vision device 10. In the embodiment shown here, the topology 90 at the inner side 92 of the spherical contact area 86 is formed by a plurality of centrally arranged ribs 91. The spherical contact area 86 can provide better friction with a certain graining, texture, ribbed or dotted patterns (not shown) that can be manufactured directly by a plastic injection moulding process.

Figure 47:
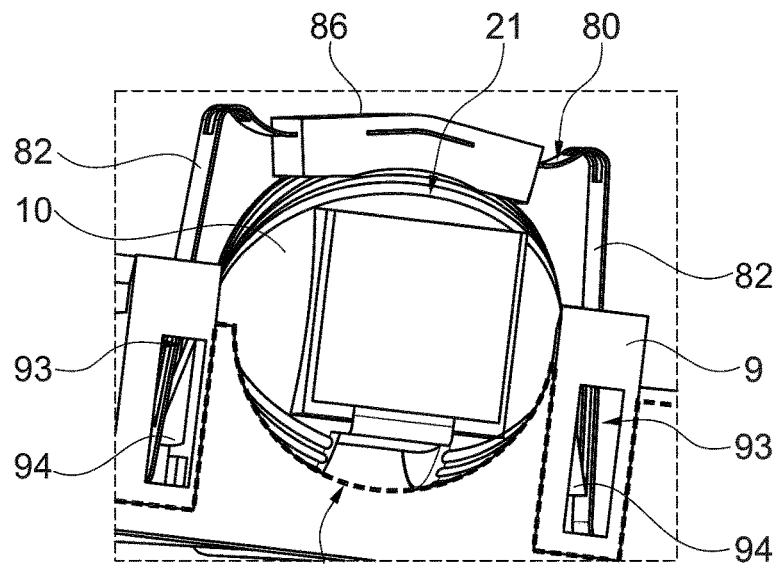
FIG. 47 is a perspective view, wherein the overmold of the hair pin spring comes into contact with the vision device.
Figure 48:
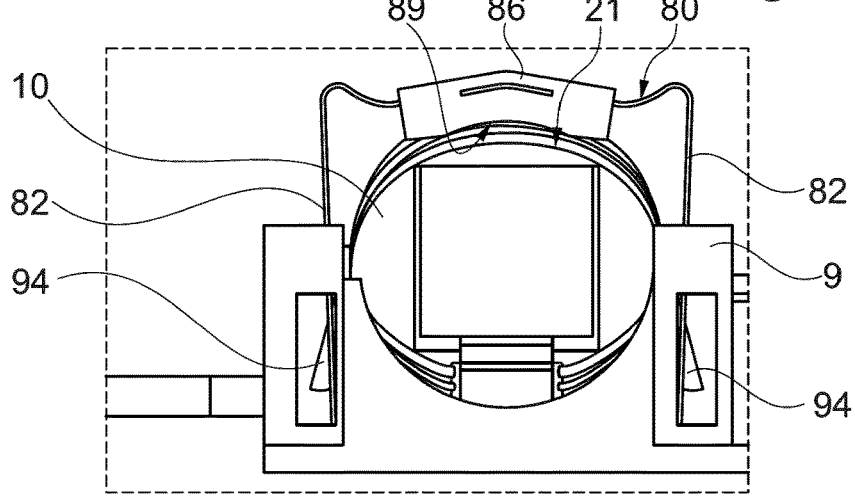
FIG. 48 is a view, wherein the hair pin spring is in firm contact with the vision device.
Figure 49:
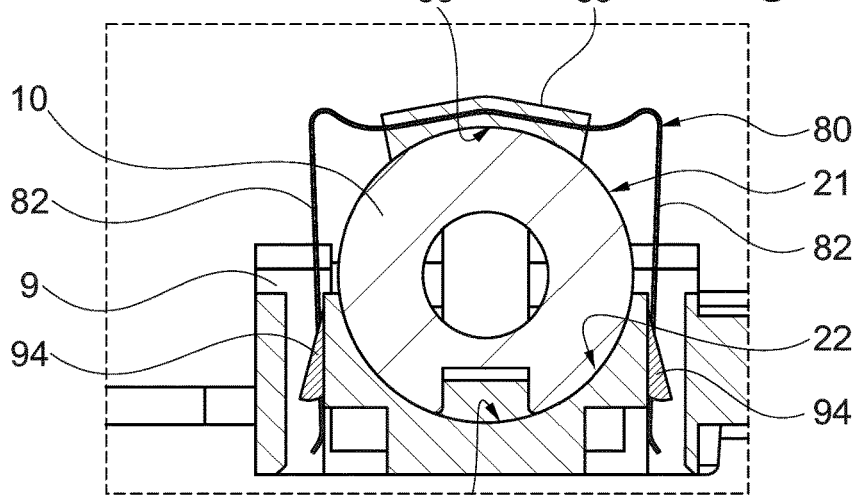
FIG. 49 is a sectional view of the hair pin spring in form fit contact with the vision device.

FIGS. 47 to 49 show the stages, wherein the overmolded part 86, its spherical contact area 89, of the hair pin spring 80 comes into contact with the first spherical outer contour 21 of the vision device 10. The arms 82 of the of the hair pin spring 80 are inserted into a respective channel 93 of the housing base 9. Optionally a minimal force may be exerted on the vision device 10 via a gripper (not shown), so that the vision device 10, positioned in the receptacle 16, does not move during the insertion and mounting of the hair pin spring 80 in the channels 93. The hair pin spring 80 is lowered to the vision device and the spring arms 82 start engaging a ramp 94 in each channel 93. As shown in FIG. 48, the hair pin spring 80 is in the final position, wherein each ramps 94 on the channels 93 of the housing base 9 reach through the lug 87 (see FIG. 44) of each arm 82 of the hair pin spring 80. The spherical contact area 89 of the overmolded part 86 reaches the first spherical outer contour 21 of the vision device 10 in form and force fitting contact with the outer contour 21 of the vision device 10 while the second spherical outer contour 22 of the vision device 10 is at least in form fitting contact with the spherical portion 32 of the receptacle 16.

Finally, the housing cover 8 (not shown here) is lowered down unto the housing base 9 in order to complete the outer housing 7. The housing cover 8 is fixed to housing base 9 by whatever conventional means. The vision device 10 can be of the embodiments shown in FIG. 5, 6 or 30.

Figure 50:
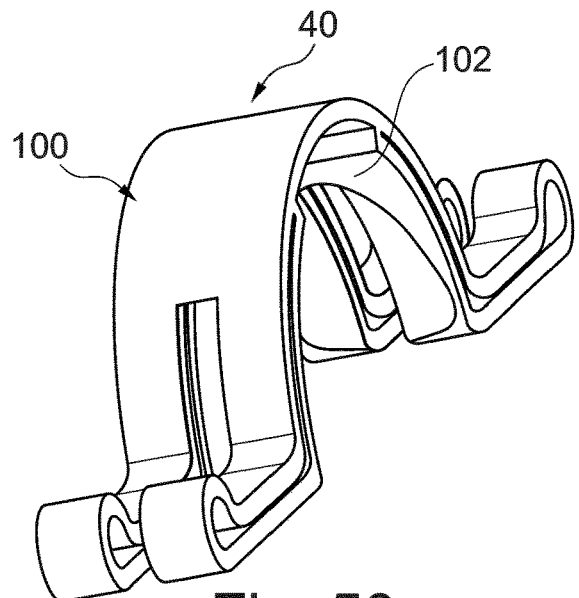
FIG. 50 is a perspective view of a flexible coil solution for clamping the vision device.
Figure 51:
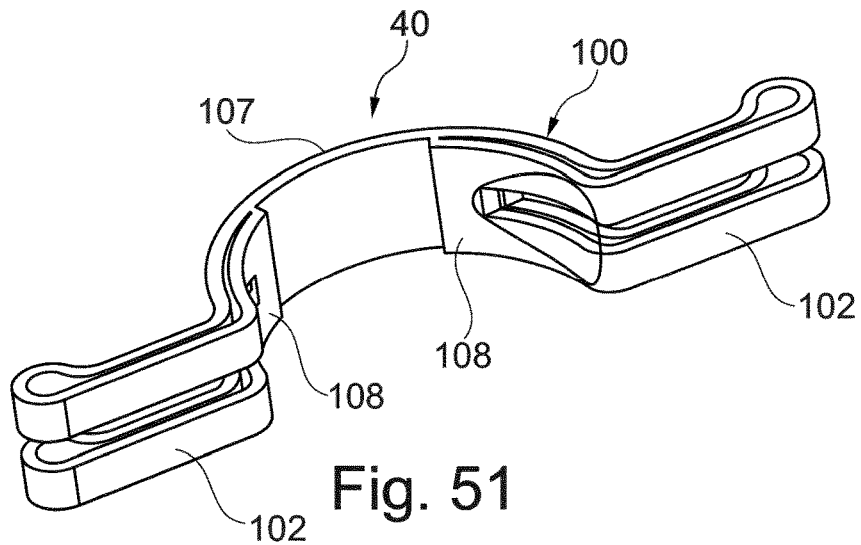
FIG. 51 is a perspective view from below of the flexible coil solution for clamping the vision device.

FIGS. 50 and 51 show a further embodiment of the mounting element 40. The mounting element 40 is sheet metal spring 100 with no overmold. The sheet metal spring 100 has a lower side which is split in this embodiment in two halves. The lips 102 are formed such that they will embrace the first spherical outer contour 21 of the vision device when mounted to the housing base 9. (see FIGS. 52 and 53).

Figures 52, 53:
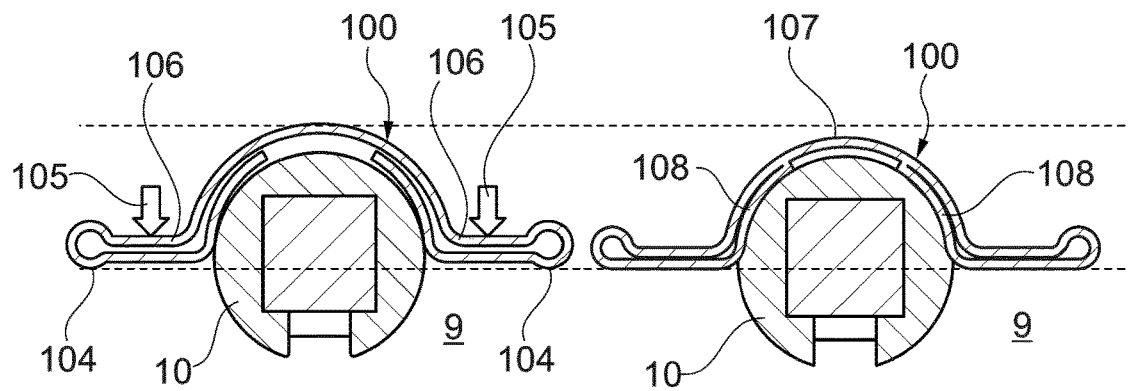
FIG. 52 is the flexible coil solution before clamping of the vision device.
FIG. 53 is the flexible coil solution after clamping of the vision device.

FIG. 52 show the mounting element 40, which is in this embodiment the sheet metal spring 100 as shown in FIGS. 50 and 51, before clamping of the vision device 10. In FIG. 53 the vision device 10 is clamped by the sheet metal spring 100. The embodiment if the sheet metal spring 100 (flexible coil solution) does not need lugs as required in the embodiment of mounting element 40 shown in FIGS. 44 to 46. This solution of mounting the vision device 10 is particularly valuable because it does not require any lug geometry on itself, or a snap geometry on the housing base 9.

As shown in FIG. 52 the sheet metal spring 100 is seated on the initial sitting zones 104 on the housing base 9. Then the upper lip 106 is pushed down as per arrows 105. The pushing down can be done for example by a screw (not shown). In doing so, the outer half ring 107 is pushed down on the inner quarter rings 108, that in turn embrace and clamp on the vision device 10. The mounting is particularly advantageous when the pushing down geometries are belonging to the housing cover 8 (not shown). Then no additional fixation items are needed (for example screws).

As well, the mounting element 40 (lamellar spring) may be obtained fully by plastic injection. Such a plastic solution is advantageous because it allows easy manufacturing of a spherical contact geometry for the vision device 10, however the plastic solution may be limited in clamping force.

Figure 54:
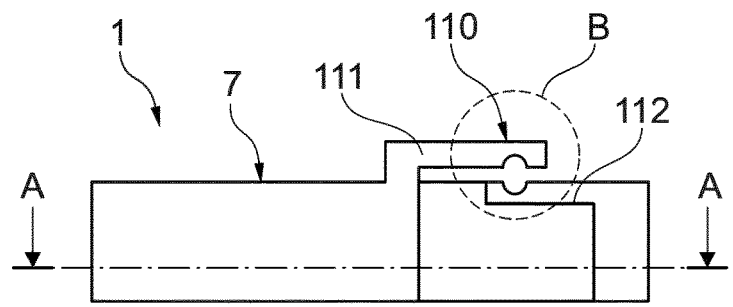
FIG. 54 is a side view of a further embodiment of the outer housing for the driver monitoring system.

FIG. 54 is a side view of a further embodiment of the outer housing 7 for the driver monitoring system 1. The outer housing 7 is designed such that a pincer 110 is provided for mounting the vision device 10 which is an infrared module 12 (not shown here) outside form the h outer housing 7. The pincer 110 has an upper part 111 and a lower part 112. With this arrangement, the cooling and orientation of the infrared module 12 is no longer part of the outer housing 7. The pincer 110 specially designed for retaining the infrared module 12 (see FIGS. 7A to 7C). The pincer 110 is positioned, at best on the edge of the outer housing 7 to optimize the cooling of the infrared module 12. The outer housing 7 is fit for plastic injection or die casting (metal).

Figure 55:
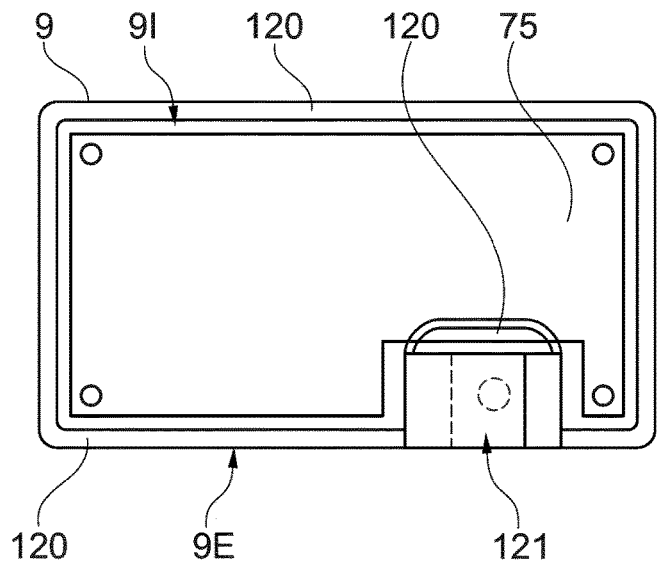
FIG. 55 is a top view into the housing base.
Figure 56:
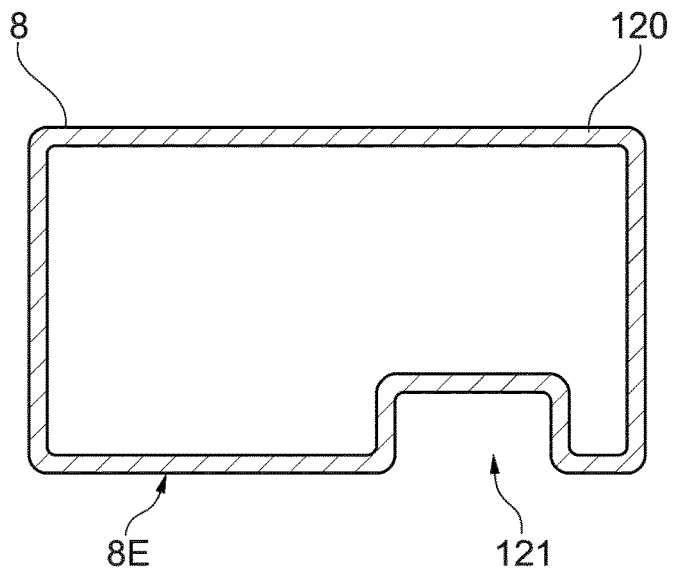
FIG. 56 is a top view into the housing base along line A-A in FIG. 54.

FIG. 55 is a top view into the housing base 9 of FIG. 54, and FIG. 56 is a view into the housing cover 8 along line A-A in FIG. 54. The housing base 9 holds in the inner portion 9I the main printed circuit board 75. The edge 9E of the housing base 9 and/or the edge 8E of the housing cover 8 can be provided with a sealing 120. The only difference from the housings described above is a formed area for a window 122 for the infrared module 12.

Figure 57:
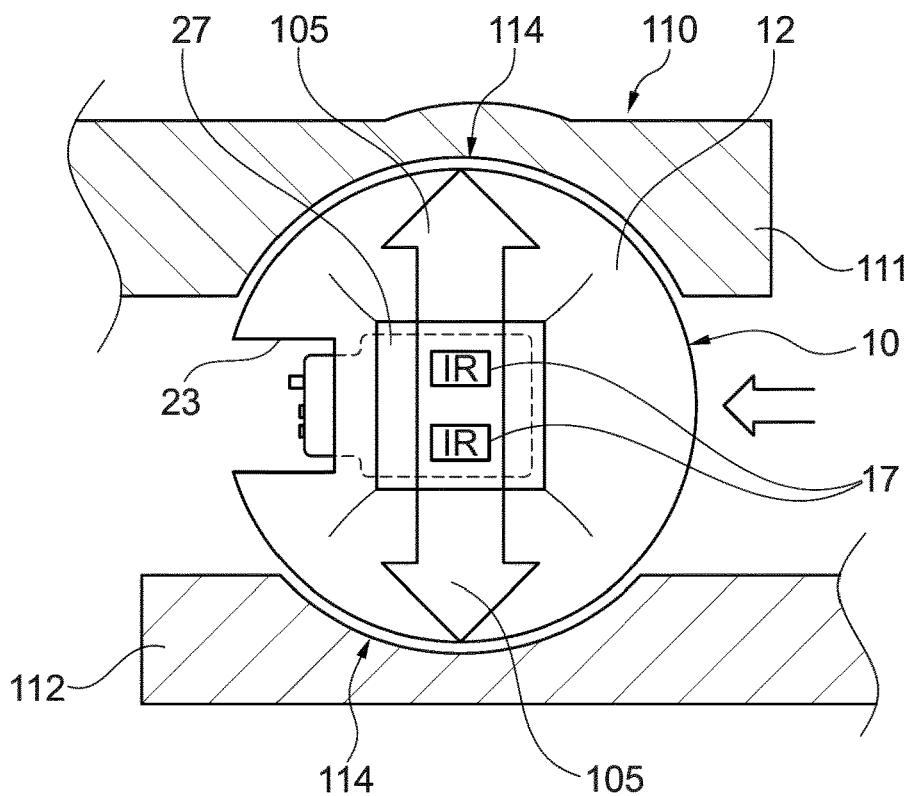
FIG. 57 is a detailed view of the pincer technology for clamping the vision device (infrared module).

FIG. 57 is a detailed view of the area marked with the circle B in FIG. 54 of the pincer 110 for clamping the vision device 10 which is an infrared module 12.

The infrared module 12 is hosting the flexible printed circuit board 27, wherein IR-diodes 17 are placed on the flexible printed circuit board 27 and cooling of the IR diodes 17 is carried out through the flexible printed circuit board 27. Through the channel 23 the flexible band cable 24 (see FIG. 7B or 7C) is guided the toward the main printed circuit board 75 (see FIG. 55). During the mounting process, the infrared module 12 can be oriented and reoriented with respect to the outer housing 7. The clamping of the infrared module 12 is cone by the pincer 110 of the outer housing 7, so that unintended rotation is not possible.

The arrows 105 in FIG. 57 show possible faces 114 of the upper part 111 and the lower part 112 of the pincer 110 to be used in insertion, orientation or reorientation of the infrared module 12. The contact surface of the infrared module 12 with the faces 114 of the upper part 111 and the lower part 112 of the pincer 110 is generally spherical and serves as counter geometry for clamping with the pincer 110.

The infrared module 12 shall be made of a good heat conducting material, for example aluminium. In addition, the topology of the infrared module 12 (see FIGS. 6A and 6B) has multiple venting holes, which may reduce weight but more importantly increase a convection area.

Figure 58:
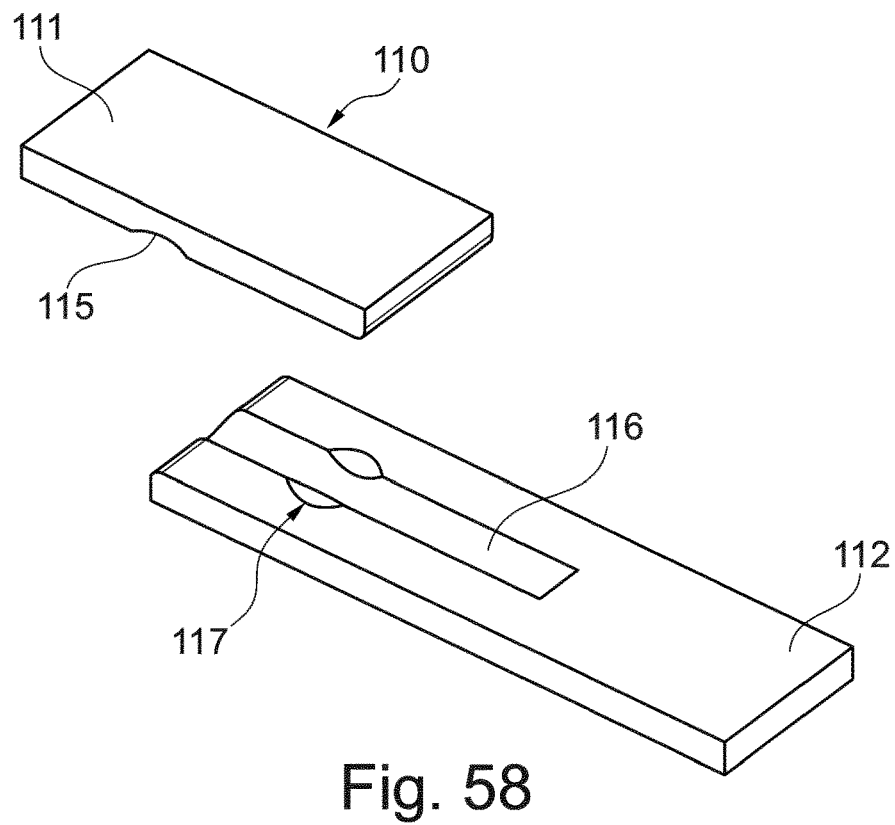
FIG. 58 shows the orientation of the pincer elements, wherein the topology design of the lower part of the pincer is visible.
Figure 59:
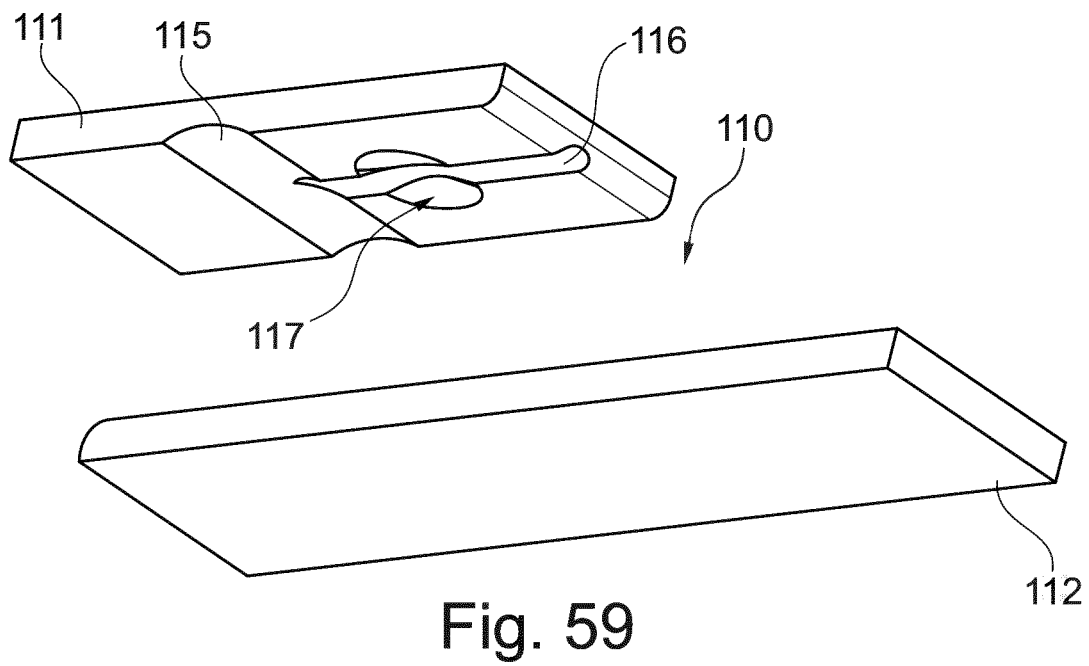
FIG. 59 shows the orientation of the pincer elements, wherein the topology design of the lower pincer element is visible.

FIG. 58 shows the orientation of the upper part 111 and the lower part 112 of the pincer 110, wherein the topology design of the lower part 112 of the pincer 110 is visible. FIG. 59 shows the orientation of the upper part 111 and the lower part 112 of the pincer 110, wherein the topology design of the upper part 112 of the pincer 110 is visible. The upper part 111 of the pincer 110 has a recess 115 for extraction of a mounting tool (not shown) for the infrared module 12. The upper part 111 and the lower part 112 of the pincer 110 have a guiding groove 116 formed which is used for the mounting tool (not shown). Both, the upper part 111 and the lower part 112 of the pincer 110 have a spherical topology 117 formed, which is in form and force fitting contact with the infrared module 12.

Figure 60:
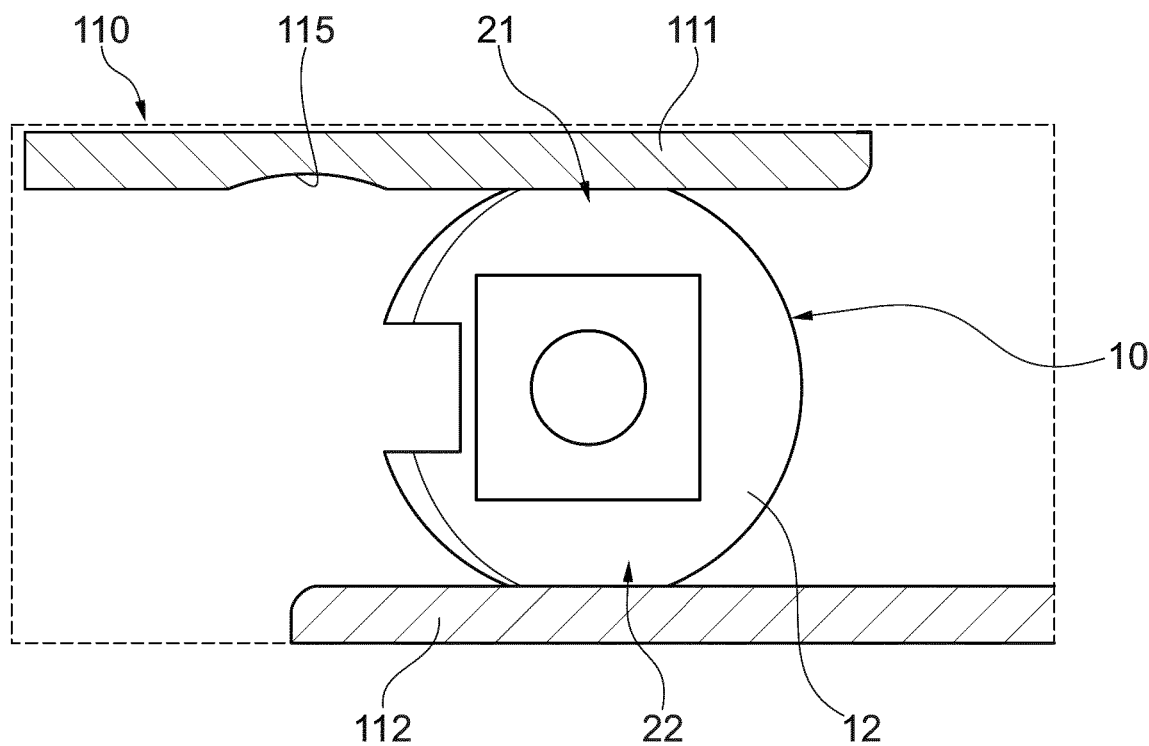
FIG. 60 shows the vision device (infrared module) clamped between the upper and the part of the pincer.

FIG. 60 shows the vision device 10 (infrared module 12) clamped between the upper part 111 and the lower part 112 of the pincer 110. The infrared module 12 is clamped between the upper part 111 and the lower part 112 of the pincer 110 and thereby the first spherical outer contour 21 and the second spherical outer contour 22 of the infrared module 12 are if form and force fitting contact with the spherical topology 117 of the upper part 111 and the lower part 112 of the pincer 110 (see FIGS. 58 and 59).

Figure 61:
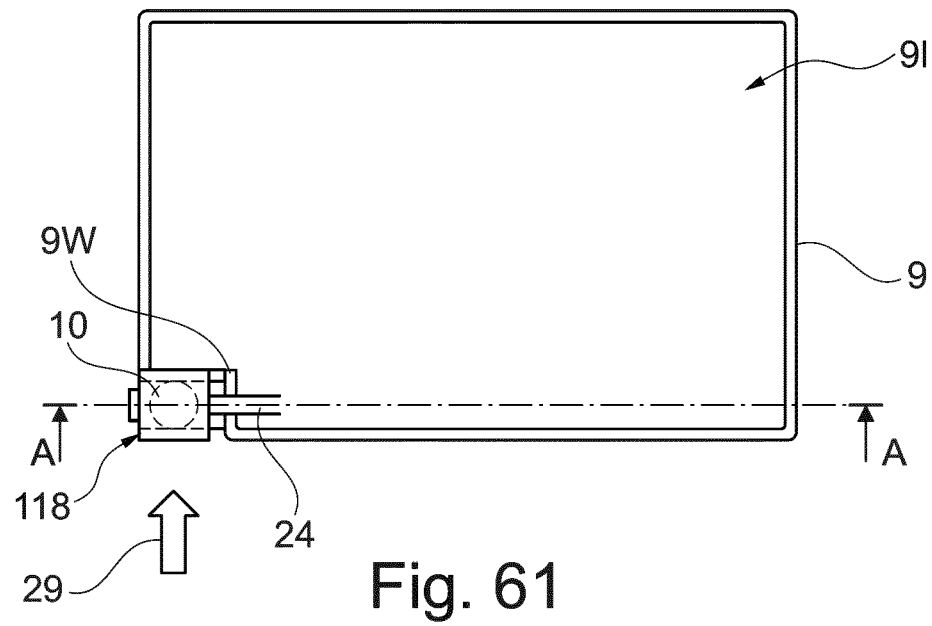
FIG. 61 shows an embodiment for installation of the vision device (infrared module).
Figure 62:
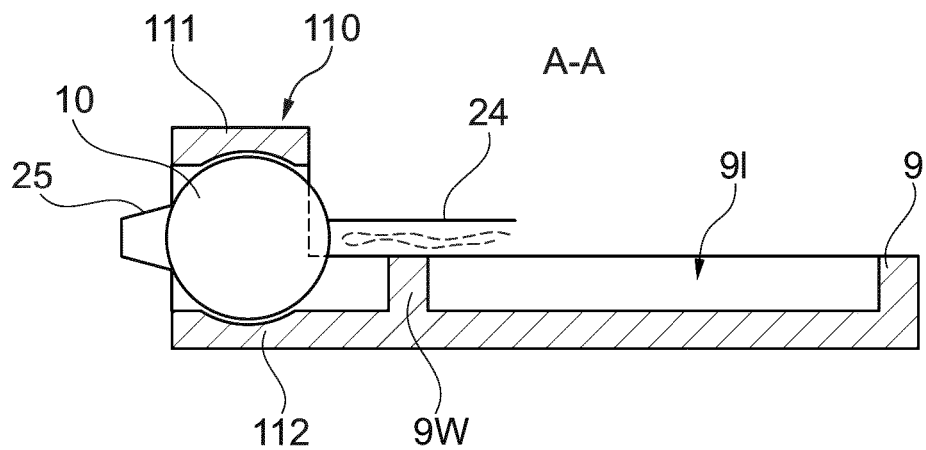
FIG. 62 shows a sectional view along line A-A of the embodiment shown in FIG. 61.
Figure 63:
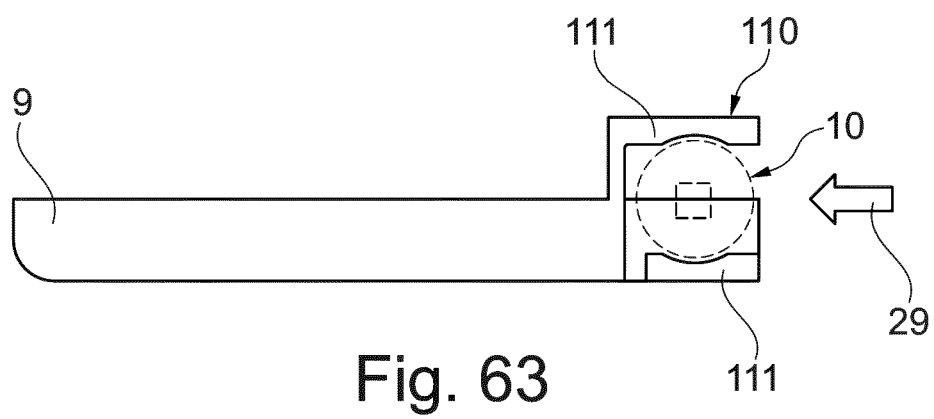
FIG. 63 shows a view along an arrow as shown in FIG. 61.

FIGS. 61 to 63 show a further embodiment for the installation of the vision device 10 (infrared module 12). According to the embodiment shown here the installation of the vision device 10 is at the corner 118 of the housing base 9. As can be clearly seen from FIG. 62 (view along cutting line A-A in FIG. 61), the vision device 10 is held as well by a pincer 110 comprising the upper part 111 and the lower part 112. Here the upper part 111 and the lower part 112 are no longer parallel. The upper part 111 and the lower part 112 be at an angle dictated by the outline of the housing base 9. as for instance 90 degrees. The arrow 29 in FIGS. 61 and 63 shows the insertion direction for the vision device 10 between the upper part 111 and the lower part 112 of the pincer 110. The band cable 24 is guides through wall 9W into the inner portion 9I of the housing base 9. The neck 25 of the vision device 10 is pointing to the outside of the outer housing 7.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Accordingly, the scope of the invention should be limited only by the claims appended hereto.

The invention claimed is:

1. A driver monitoring system, comprising,
at least one vision device positioned in or at an outer housing and pointing to an outside of the outer housing, wherein the outer housing is defined by a housing cover and a housing base wherein the housing base has at least one receptacle which defines a spherical portion,
a vision device housing having a first spherical outer contour and a second spherical outer contour, wherein the first spherical outer contour and the second spherical outer contour cooperate with the housing base and with a mounting element to provide a form and force fitting mount of the vision device in the outer housing, wherein the second spherical outer contour of the vison device is in a form fitting contact with the spherical portion of the least one receptacle and wherein the least one receptacle has a central pin which reaches into a channel provided at the second spherical outer contour of the vision device housing.

2. The driver monitoring system as claimed in claim 1, wherein the first spherical outer contour and the second spherical outer contour of the vision device housing are smooth or have an array of shallow grooves formed on at least one of the first spherical outer contour and the second spherical outer contour.

3. The driver monitoring system as claimed in claim 1, wherein the vision device is a vision camera or an infrared module.

4. The driver monitoring system as claimed in claim 1, wherein the mounting element of the driver monitoring system is in a form and force fitting contact with the first spherical outer contour of the vision device housing.

5. A driver monitoring system comprising, at least one vision device positioned in or at an outer housing and pointing to an outside of the outer housing, wherein the outer housing is defined by a housing cover and a housing base,
a vision device housing having a first spherical outer contour and a second spherical outer contour, wherein the first spherical outer contour and the second spherical outer contour cooperate with the housing base and with a mounting element to provide a form and force fitting mount of the vision device in the outer housing, wherein the mounting element is in a form and force fitting contact with the first spherical outer contour of the vision device housing, and wherein the mounting element is a flange of the housing cover having a flexible area with a topology mating with the first spherical outer contour of the vision device when the housing cover and the housing base are joined.

6. The driver monitoring system as claimed in claim 5, wherein the housing base has at least one receptacle which defines a spherical portion, wherein the second spherical outer contour of the vison device is in form fitting contact with the spherical portion of the least one receptacle.

7. The driver monitoring system as claimed in claim 5, wherein the least one receptacle has a central pin which reaches into a channel provided at the second spherical outer contour of the vision device housing.

8. The driver monitoring system as claimed in claim 5, wherein the topology mating the first spherical outer contour of the vision device is present when an elongation of the flexible area is joined with a clinching dome of the housing base.

9. The driver monitoring system as claimed in claim 5, wherein the mounting element has a plurality of flexible fingers having a tip portion, wherein the tip portions are in form and force fitting contact with at least one shallow groove on the first spherical outer contour of the vision device when the housing cover is joined with the housing base.

10. The driver monitoring system as claimed in claim 5, wherein the mounting element has oppositely arranged claw flanges, wherein the claw flanges are in form and force fitting contact with the first spherical outer contour of the vision device when the housing cover is joined with the housing base.

11. The driver monitoring system as claimed in claim 9, wherein the mounting element is attached via a first flexible strip to the housing cover, and a second flexible strip of the mounting element is attached to a fixing which is mounted to the housing base.

12. The driver monitoring system as claimed in claim 5, wherein the mounting element is a hair pin spring with a spherical contact area which is in a form and force fitting contact with the first spherical outer contour of the vision device when the hair pin spring is mounted to the housing base.

13. The driver monitoring system as claimed in claim 5, wherein the mounting element is a sheet spring with an outer half ring and two inner quarter rings, wherein the inner quarter rings embrace the first spherical outer contour of the vision device when the sheet spring is pushed down to the housing base.

14. The driver monitoring system as claimed in claim 5, wherein the vision device is an infrared module which is mounted in a form and force fitting manner in the outer housing or outside the outer housing.

15. The driver monitoring system as claimed in claim 14, wherein an upper part and a lower part of a pincer have a spherical topology, which are in form and force fitting contact with the first spherical outer contour and the second spherical outer contour of the infrared module.

* * * * *